United States Patent
Lardo et al.

(10) Patent No.: US 6,675,033 B1
(45) Date of Patent: Jan. 6, 2004

(54) MAGNETIC RESONANCE IMAGING GUIDEWIRE PROBE

(75) Inventors: Albert C. Lardo, Baldwin, MD (US); Xiaoming Yang, Baltimore, MD (US); Ergin Atalar, Columbia, MD (US); Parag Karmarkar, Eliott City, MD (US); Elliott R. McVeigh, Potomac, MD (US); Henry R. Halperin, Baltimore, MD (US); Christine Enger McNamara, Chelmsford, MA (US); Paul A. Bottomley, Columbia, MD (US)

(73) Assignees: Johns Hopkins University School of Medicine, Baltimore, MD (US); Surgi-Vision, Inc., Chelmsford, MA (US)

( * ) Notice: Subject to any disclaimer, the term of this patent is extended or adjusted under 35 U.S.C. 154(b) by 0 days.

(21) Appl. No.: 09/536,090

(22) Filed: Mar. 24, 2000

Related U.S. Application Data

(60) Provisional application No. 60/129,364, filed on Apr. 15, 1999.

(51) Int. Cl.[7] .............................................. A61B 5/055
(52) U.S. Cl. ....................... 600/410; 600/417; 600/423; 324/300; 324/302; 324/309
(58) Field of Search ................................ 600/407, 410, 600/423, 417; 324/300, 301, 302, 309

(56) References Cited

U.S. PATENT DOCUMENTS

| | | |
|---|---|---|
| 3,342,175 A | 9/1967 | Bulloch |
| 4,431,005 A | 2/1984 | McCormick ................ 128/656 |
| 4,445,501 A | 5/1984 | Bresler ....................... 128/1.5 |
| 4,554,929 A | 11/1985 | Samson et al. ............. 128/772 |
| 4,572,198 A | 2/1986 | Codrington ................ 128/653 |
| 4,643,186 A | 2/1987 | Rosen et al. ............. 128/303.1 |
| 4,672,972 A | 6/1987 | Berke ......................... 128/653 |
| 4,682,125 A * | 7/1987 | Harrison et al. ............. 324/318 |

(List continued on next page.)

FOREIGN PATENT DOCUMENTS

| | | |
|---|---|---|
| EP | 0 466 424 A1 | 1/1992 |
| EP | 0 557 127 A2 | 8/1993 |
| EP | 0 659 385 A1 | 6/1995 |
| EP | 0 557 127 A3 | 3/1996 |
| EP | 0 768 539 A2 | 4/1997 |
| EP | 0 850 595 A1 | 7/1998 |
| EP | 0 908 739 A2 | 4/1999 |
| JP | 6[1994]-70902 | 3/1994 |
| WO | WO 98/52064 | 11/1998 |
| WO | WO 98/52461 | 11/1998 |
| WO | WO 99/18852 | 4/1999 |
| WO | WO 99/27390 | 6/1999 |
| WO | WO 99/59479 | 11/1999 |
| WO | WO 00/64003 A | 10/2000 |
| WO | WO 00/64003 | 10/2000 |

OTHER PUBLICATIONS

Lardo, A.C.; "Real–Time Magnetic Resonance Imaging: Diagnostic and Interventional Applications", Pediatric Cardiology, Springer–Verlag, NY, US., vol. 21, No. 1: 80–98, (Jan. 2000).
Form PCT/ISA/210, International Search Report for PCT/US 01/03346 (Nov. 5, 2001), Applicant: Surgi–Vision, Inc.
Ladd et al.; "Guidewire Antennas for MR Fluoroscopy", Magnetic Resonance in Medicine, Academic Press, Duluth, MN, US., vol. 37(6): 891–897, (Jun. 1, 1997).

(List continued on next page.)

*Primary Examiner*—Marvin M. Lateef
*Assistant Examiner*—Jeoyuh Lin
(74) *Attorney, Agent, or Firm*—Foley Hoag LLP

(57) ABSTRACT

The invention describes a system, method, and means for an MRI guidewire that can be visible on an MRI, can act as an antenna and receive MRI signals from surrounding subject matter, and can allow the use of multiple interventional tools without removal of the guidewire from a subject.

73 Claims, 19 Drawing Sheets

U.S. PATENT DOCUMENTS

| | | |
|---|---|---|
| 4,766,381 A | 8/1988 | Conturo et al. ............. 324/309 |
| 4,776,341 A | 10/1988 | Bachus et al. .............. 128/653 |
| 4,791,372 A | 12/1988 | Kirk et al. ................... 324/318 |
| 4,793,356 A | 12/1988 | Misic et al. ................ 128/653 |
| 4,813,429 A | 3/1989 | Eshel et al. ................. 128/736 |
| 4,823,812 A | 4/1989 | Eshel et al. ................. 128/804 |
| 4,858,613 A | 8/1989 | Fry et al. ............... 128/660.03 |
| 4,859,950 A * | 8/1989 | Keren ........................ 324/318 |
| 4,897,604 A | 1/1990 | Carlson et al. ............. 324/318 |
| 4,922,204 A | 5/1990 | Duerr et al. ................ 324/322 |
| 4,932,411 A | 6/1990 | Fritschy et al. ............. 128/653 |
| 4,960,106 A | 10/1990 | Kubokawa ..................... 128/6 |
| 5,019,075 A | 5/1991 | Spears et al. .................... 606/7 |
| 5,035,231 A | 7/1991 | Kubokawa et al. ............ 128/6 |
| 5,050,607 A | 9/1991 | Bradley et al. ......... 128/653 A |
| 5,090,959 A | 2/1992 | Samson et al. ............... 604/96 |
| 5,095,911 A | 3/1992 | Pomeranz ............. 128/662.06 |
| 5,099,208 A | 3/1992 | Fitzpatrick et al. ......... 324/312 |
| 5,167,233 A | 12/1992 | Eberle et al. .......... 128/662.06 |
| 5,170,789 A | 12/1992 | Narayan et al. ......... 128/653.5 |
| 5,190,046 A | 3/1993 | Shturman .............. 128/662.06 |
| 5,211,165 A | 5/1993 | Dumoulin et al. ....... 128/653.1 |
| 5,211,166 A | 5/1993 | Sepponen |
| 5,217,010 A | 6/1993 | Tsitlik et al. ......... 128/419 PG |
| 5,260,658 A | 11/1993 | Greim et al. ............... 324/322 |
| 5,270,485 A | 12/1993 | Jacobsen ................... 174/15.1 |
| 5,271,400 A | 12/1993 | Dumoulin et al. ....... 128/653.2 |
| 5,293,872 A | 3/1994 | Alfano et al. ............... 128/664 |
| 5,294,886 A | 3/1994 | Duerr ........................ 324/318 |
| 5,307,808 A | 5/1994 | Dumoulin et al. ....... 128/653.2 |
| 5,307,814 A | 5/1994 | Kressel et al. ........... 128/653.5 |
| 5,318,025 A | 6/1994 | Dumoulin et al. ....... 128/653.2 |
| 5,323,778 A | 6/1994 | Kandarpa et al. ........ 128/653.2 |
| 5,348,010 A | 9/1994 | Schnall et al. ........... 128/653.2 |
| 5,352,979 A | 10/1994 | Conturo ..................... 324/307 |
| 5,355,087 A | 10/1994 | Claiborne et al. .......... 324/322 |
| 5,358,515 A | 10/1994 | Hürter et al. ............... 607/101 |
| 5,365,928 A | 11/1994 | Rhinehart et al. ....... 128/653.5 |
| 5,370,644 A | 12/1994 | Langberg ..................... 606/33 |
| 5,372,138 A | 12/1994 | Crowley et al. ....... 128/662.06 |
| 5,375,596 A | 12/1994 | Twiss et al. ............. 128/653.1 |
| 5,400,787 A | 3/1995 | Marandos ................ 128/653.5 |
| 5,411,476 A | 5/1995 | Abrams et al. ............... 604/95 |
| 5,413,104 A | 5/1995 | Buijs et al. .............. 128/653.5 |
| 5,419,325 A | 5/1995 | Dumoulin et al. ....... 128/653.2 |
| 5,421,338 A | 6/1995 | Crowley et al. ....... 128/662.06 |
| 5,429,132 A | 7/1995 | Guy et al. ............... 128/653.1 |
| 5,435,302 A | 7/1995 | Lenkinski et al. .......... 600/422 |
| 5,437,277 A | 8/1995 | Dumoulin et al. ....... 128/653.1 |
| 5,439,000 A | 8/1995 | Gunderson et al. ......... 128/664 |
| 5,443,066 A | 8/1995 | Dumoulin et al. ....... 128/653.1 |
| 5,443,489 A | 8/1995 | Ben-Haim ................. 607/115 |
| 5,447,156 A | 9/1995 | Dumoulin et al. ....... 128/653.2 |
| 5,451,232 A | 9/1995 | Rhinehart et al. .......... 606/192 |
| 5,451,774 A | 9/1995 | Jacobsen ............... 250/227.24 |
| 5,462,055 A | 10/1995 | Casey et al. ............. 128/653.5 |
| 5,476,095 A | 12/1995 | Schnall et al. ........... 128/653.2 |
| 5,498,261 A | 3/1996 | Strul ........................... 606/29 |
| 5,507,743 A | 4/1996 | Edwards et al. .............. 606/41 |
| 5,512,825 A | 4/1996 | Atalar et al. ................ 324/309 |
| 5,520,644 A | 5/1996 | Imran .......................... 604/95 |
| 5,524,630 A | 6/1996 | Crowley ................ 128/662.06 |
| 5,540,679 A | 7/1996 | Fram et al. ................... 606/27 |
| 5,558,093 A | 9/1996 | Pomeranz ............. 128/660.03 |
| 5,578,008 A | 11/1996 | Hara ........................... 604/96 |
| 5,588,432 A | 12/1996 | Crowley ................ 128/660.03 |
| 5,598,097 A | 1/1997 | Scholes et al. ............. 324/316 |
| 5,609,606 A | 3/1997 | O'Boyle ..................... 606/194 |
| 5,611,807 A | 3/1997 | O'Boyle ..................... 606/169 |
| 5,623,241 A | 4/1997 | Minkoff ..................... 335/296 |
| 5,660,180 A | 8/1997 | Malinowski et al. .. 128/660.03 |
| 5,682,897 A | 11/1997 | Pomeranz .............. 128/662.06 |
| 5,699,801 A | 12/1997 | Atalar et al. ............. 128/653.2 |
| 5,715,825 A | 2/1998 | Crowley ................ 128/602.06 |
| 5,728,079 A | 3/1998 | Weber et al. ................ 604/280 |
| 5,738,632 A | 4/1998 | Karasawa ................... 600/410 |
| 5,775,338 A | 7/1998 | Hastings ........................ 128/898 |
| 5,792,055 A * | 8/1998 | McKinnon .................. 600/410 |
| 5,833,608 A | 11/1998 | Acker ........................ 600/409 |
| 5,833,632 A | 11/1998 | Jacobsen et al. ............ 600/585 |
| 5,840,031 A | 11/1998 | Crowley ..................... 600/440 |
| 5,868,674 A | 2/1999 | Glowinski et al. .......... 600/410 |
| 5,916,162 A | 6/1999 | Snelten et al. .............. 600/411 |
| 5,928,145 A | 7/1999 | Ocali |
| 5,938,609 A | 8/1999 | Pomeranz ................... 600/439 |
| 5,938,692 A | 8/1999 | Rudie ......................... 607/101 |
| 5,964,705 A | 10/1999 | Truwit et al. ............... 600/423 |
| 5,968,052 A | 10/1999 | Sullivan, III et al. ....... 606/108 |
| 6,004,269 A | 12/1999 | Crowley et al. ............ 600/439 |
| 6,011,995 A | 1/2000 | Guglielmi et al. ............ 607/99 |
| 6,171,240 B1 | 1/2000 | Young et al. ............... 600/410 |
| 6,019,737 A | 2/2000 | Murata ....................... 600/585 |
| 6,026,316 A | 2/2000 | Kucharczyk et al. ....... 600/420 |
| 6,031,375 A | 2/2000 | Atalar et al. ................. 324/307 |
| 6,032,078 A | 2/2000 | Rudie ......................... 607/101 |
| 6,051,974 A | 4/2000 | Reisker et al. .............. 324/318 |
| 6,058,323 A | 5/2000 | Lemelson ................... 600/408 |
| 6,061,587 A | 5/2000 | Kurcharczyk et al. ...... 600/411 |
| 6,064,203 A | 5/2000 | Bottomley ................... 324/309 |
| 6,078,831 A | 6/2000 | Belef et al. ................. 600/424 |
| 6,104,943 A | 8/2000 | Frederick et al. ........... 600/410 |
| 6,171,241 B1 | 1/2001 | McVeigh et al. ........... 600/410 |
| 6,188,219 B1 | 2/2001 | Reeder et al. ............... 324/307 |
| 6,233,474 B1 | 5/2001 | Lemelson ................... 600/411 |
| 6,263,229 B1 | 7/2001 | Atalar et al. ................ 600/423 |
| 6,272,370 B1 * | 8/2001 | Gillies et al. ............... 324/309 |
| 6,351,124 B1 * | 2/2002 | Vester et al. ................ 324/318 |
| 6,408,202 B1 * | 6/2002 | Lima et al. .................. 324/307 |
| 6,549,800 B1 | 4/2003 | Atalar et al. |
| 2001/0056232 A1 | 12/2001 | Lardo et al. ................ 600/423 |
| 2002/0040185 A1 | 4/2002 | Atalar et al. ................ 600/423 |
| 2002/0045816 A1 | 4/2002 | Atalar et al. ................ 600/423 |
| 2002/0097050 A1 | 7/2002 | Kellman et al. ............ 324/309 |
| 2002/0161421 A1 | 10/2002 | Lee et al. .................... 607/116 |
| 2002/0177771 A1 | 11/2002 | Guttman et al. ............ 600/410 |
| 2003/0028094 A1 | 2/2003 | Kumar et al. ............... 600/410 |
| 2003/0028095 A1 | 2/2003 | Tulley et al. ............... 600/422 |
| 2003/0050557 A1 | 3/2003 | Susil et al. .................. 600/424 |

OTHER PUBLICATIONS

Martin et al.; "An Expandable Intravenous RF Coil for Imaging the Artery Wall", Proceeding of the International Society for Magnetic Resonance In Medicine, Fourth Scientific Meeting and Exhibition, New York, USA Apr. 27–May 3, 1996, vol. 1, p. 402.

Quick et al; "Vascular Stents as RF–Antennas for Intravascular MR–Guidance and– Imaging", Proceedings of the International Society for Magnetic Resonance in Medicine, Seventh Scientific Meeting and Exhibition, Philadelphia, Pennsylvania, USA May 22–28, 1999, vol. 1, p. 577.

Atalar et al.; "High Resolution Intravascular MRI and MRS using a Catheter Receiver Coil,", Magnteic Resonance in Medicine, 36:596–605 (1996).

Edelman et al.; "Magnetic Resonance Imaging" NEJM. 328: 708–716 (1993).

Farmer et al.; "Implanted Coil MR Microscopy of Renal-pathology", Magn. Reson. Med., 10: 310–323 (1989).

Garwood et al., "Magnetic Resonance Imaging with Adiabatic Using a Single Surface Coil for RF Transmission and Signal Detection", Magnetic Resonance in Medicine 9: 25–34 (1989).

Hoult et al.; "The Signal–to–Noise Ratio of the Nuclear Magnetic Resonance Experiment" J. Magn. Reson., 24: 71–85 (1976).

Hoult; "Rotating Frame Zeugmatography", Phil. Trans. R. Soc. Lond. B. 289: 543–547 (1980).

Jolesz et al. ; "Interventional Magnetic Resonance Therapy", Seminars in Interventional Radiology, 12: 20–27 (1995).

Ocali et al.; "Intravascular Magnetic Resonance Imaging Using a Loopless Catheter Antenna", MRM, 37: 112–118 (1997).

Silverman et al.; "Interactive MR–guided Biopsy in an Open configuration MR Imaging System", Radiology, 197: 175–181 (1995).

* cited by examiner

AXIAL MODE
D > λ

NORMAL MODE
D << λ

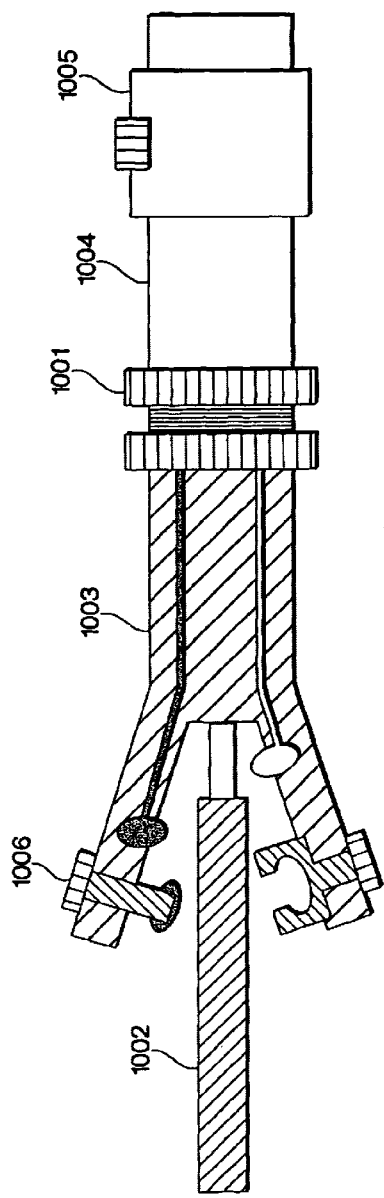
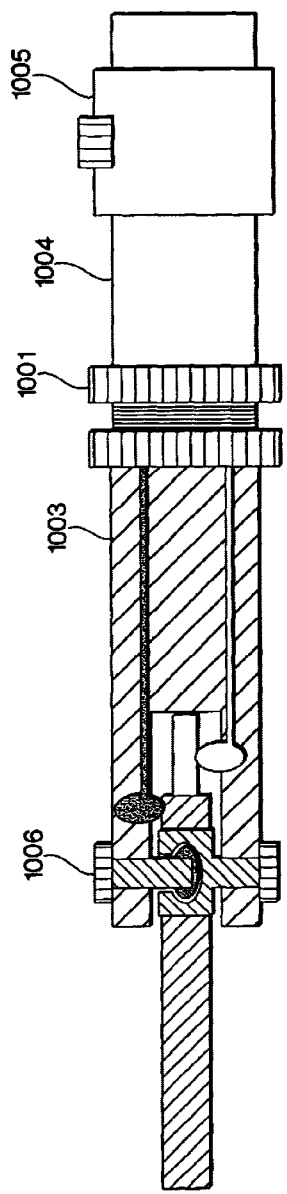
Fig. 18A
Fig. 18B

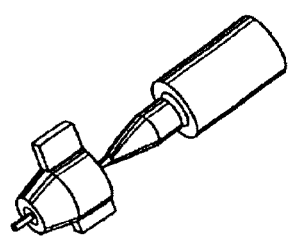
Fig. 24A
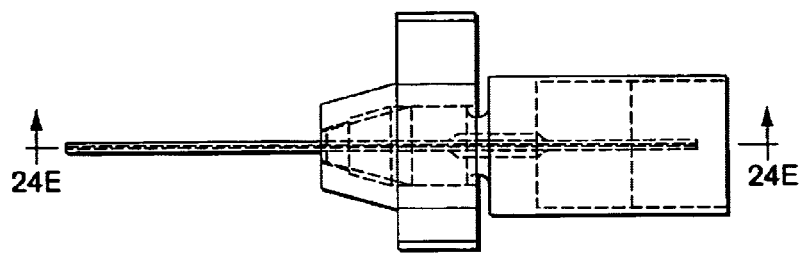
Fig. 24B
 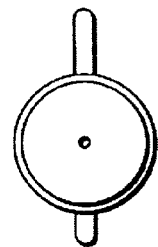
Fig. 24C          Fig. 24D
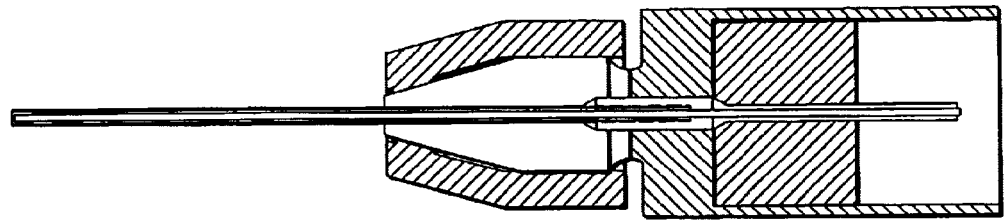
Fig. 24E

MAGNETIC RESONANCE IMAGING GUIDEWIRE PROBE

REFERENCE TO PRIOR APPLICATION

This application claims the benefit of U.S. Provisional Patent Application No. 60/129,364 filed Apr. 15, 1999, the entire disclosure of which is herein incorporated by reference.

BACKGROUND OF THE INVENTION

1. Field of the Invention

This invention relates to the field of radio frequency antennas. More particularly to the use of radio frequency antennas as guidewires used in vivo in conjunction with magnetic resonance imaging techniques.

2. Description of Related Art

Magnetic resonance imaging (MRI) is a well known, highly useful technique for imaging matter. It has particular use with imaging the human body or other biological tissue without invasive procedures or exposure to the harmful radiation or chemicals present with x-rays or CT scans. MRI uses changes in the angular momentum or "spin" of atomic nuclei of certain elements to show locations of those elements within matter. In an MRI procedure, a subject is usually inserted into an imaging machine that contains a large static magnetic field generally on the order of 0.2 to 4 Tesla although machines with higher strength fields are being developed and used. This static magnetic field tends to cause the vector of the magnetization of the atomic nuclei placed therein to align with the magnetic field. The subject is then exposed to pulses of radio frequency (RF) energy in the form of a second, oscillating, RF magnetic field having a particular frequency referred to in the art as a resonant or Larmor frequency. This frequency is equal to the rate that the spins rotate or precess.

This second field is generally oriented so that its magnetic field is oriented in the transverse plane to that of the static magnetic field and is generally significantly smaller. The second field pulls the net magnetism of the atomic nuclei off the axis of the original magnetic field. As the second magnetic field pulses, it pulls the spins off axis. When it is turned off, the spins "relax" back to their position relative to the initial magnetic field. The rate at which the spins relax is dependent on the molecular level environment. During the relaxation step, the precessing magnetization at the Larmor frequency induces a signal voltage that can be detected by antennas tuned to that frequency. The magnetic resonance signal persists for the time it takes for the spin to relax. Since different tissues have different molecular level environments, the differences in relaxation times provides a mechanism for tissue contrast in MRI.

In order to image the magnetic resonance signal it is necessary to encode the locations of the resonant spins. This is performed by applying pulse of gradient magnetic fields to the main magnetic field in each of the three dimensions. By creating this field, the location of resonant nuclei can be determined because the nuclei will resonate at a different Larmor frequency since the magnetic field they experience differs from their neighbors. The magnetic resonance (MR) image is a representation of the magnetic resonance signal on a display in two or three dimensions. This display usually comprises slices taken on an axis of interest in the subject, or slices in any dimension or combination of dimensions, three-dimensional renderings including computer generated three-dimensional "blow-ups" of two-dimensional slices, or any combination of the previous, but can comprise any display known to the art.

MR signals are very weak and therefore the antenna's ability to detect them depends on both its size and its proximity to the source of those signals. In order to improve the signal of an MRI, the antenna may be placed near or inside the subject to be imaged. Such improvements can enable valuable increases in resolution sensitivity and reduction of scan time. It may be desirable to have evidence of the MRI antenna itself on the MRI to allow the individual inserting the MRI antenna to direct where it is going and to maneuver it with aid from the MR image. Such a benefit could be useful in medical procedures where MRI is used simultaneously to track the position of an intraluminal device and to evaluate the structures surrounding the lumen. For example, an intravascular catheter could be directed through a vessel using MRI to reach a targeted area of the vessel, and the MRI apparatus could further be used to delineate the intravascular anatomy or nearby tissue to determine whether a particular therapeutic intervention would be required. Using MRI to guide the catheter and using MRI further to map out the relevant anatomy could complement conventional angiographic imaging technology within an interventional radiology or cardiology or minimally invasive imaging suite. Once the catheter is directed to the desired anatomic target under MR guidance, and once the topography or other relevant anatomy of the target lesion is depicted using MRI, the clinician can make decisions about what type of intervention would be indicated, if any, and where the intervention should be delivered.

Many conventional vascular interventional procedures use X-ray imaging technology in which guidewires and catheters are inserted into a vein or artery and navigated to specific locations in the heart for diagnostic and therapeutic procedures. Conventional X-ray guided vascular interventions, however, suffer from a number of limitations, including: (1) limited anatomical visualization of the body and blood vessels during the examination, (2) limited ability to obtain a cross-sectional view of the target vessel, (3) inability to characterize important pathologic features of atherosclerotic plaques, (4) limited ability to obtain functional information on the state of the related organ, and (5) exposure of the subject to potentially damaging x-ray radiation.

MRI techniques offer the potential to overcome these deficiencies. However, conventional guidewires are not suitable for use in MRI machines since they contain steel or magnetic materials that can cause significant image artifacts in an MRI machine and can cause injury to a patient from unintended motion due to effects of the magnetic fields or induced Ohmic heating. Additionally, guidewires made of non-magnetic materials (e.g., polymers) to cannot easily be visualized by MRI. Even those antennae which have been fabricated for use inside a human body are not useful for many types of interventional procedures. Many of these devices are simply too large to be sufficiently miniaturized to allow the placement of an interventional device simultaneously with the antenna in a small vessel without causing injury to the subject. Furthermore, many of these devices are not useful as guidewires because the antenna cannot accept the range of interventional tools that are widely used in many types of procedures without removal of the guidewire from the subject during tool transition. This includes, but is not limited to, such tools as balloon catheters for dilatation angioplasties, for stent placements, for drug infusions, and for local vessel therapies such as gene therapies; atherotomes and other devices for plaque resection and debulking;

stent placement catheters; drug delivery catheters; intraluminal resecting tools; electrophysiologic mapping instruments; lasers and radio frequency and other ablative instruments. Conventional antennas fail in this regard because they have no method for loading these devices after the antenna has been placed in the subject. The tool must instead be preloaded on the antenna, and then inserted into the subject. If a different tool is needed once the antenna has been inserted, the antenna must be entirely removed, the tool switched, and the antenna reinserted into the subject. This repositioning may require that the antenna be redirected to the lesion with the new tool in place, adding an extra, redundant step with the attendant risks of procedural complications. The more inaccessible the lesion, the greater the potential hazards that a second or subsequent positioning of the antenna may entail. In order to use a range of tools, and be useful for procedures requiring loading of multiple tools during the procedure, it is desirable that the antenna therefore be capable of loading multiple different tools after it has been placed in the subject.

SUMMARY OF THE INVENTION

To solve the guidewire visualization problem, two approaches have been proposed: passive visualization, and active visualization. With the passive visualization approach, the material of the guidewires is modified so that the catheter appears bright or dark on MR images. Unfortunately, in these techniques data acquisition speed is often limited and the position of the guidewire cannot be visualized very accurately as it depends on the signal-to-noise ratio (SNR) of a second remote detector coil (antenna) which may be sub-optimal. In addition, the modification of the material may result in image artifacts distorting the view of neighboring tissue. In the active visualization techniques, the MRI signal is received by an antenna placed at the end of the guidewire that potentially provides high SNR and spatial resolution in the vicinity of the antenna. These types of probes have also presented problems for clinical applications, since the antennas are often difficult to insert, providing proper shielding from body fluids and tissues has been difficult, and avoiding injury to patients has at times required suboptimally sized probes to be used.

It is therefore desired in the art to produce a probe that contains an antenna suitable to receive and enhance MR images, that antenna providing signal that renders it visible on an MR image and suitable for use as a guidewire.

It is further desired by the art to provide an MRI probe which is constructed of flexible material that has sufficient mechanical properties to be suitable as a guidewire and suitable electrical properties to be an antenna for MRI images rendering it visible on an MR image.

It is further desired by the art to provide an MRI probe which uses multiple different shaped whip antenna designs to allow specific uses under certain circumstances, and which can be used in a clinical environment.

It is further desired by the art to provide an MRI probe that can act as a guidewire to multiple different interventional tools without having to remove the probe from the body to change between tools.

The invention disclosed herein in one embodiment comprises a system, method, and means for providing a flexible MRI probe assembly which is capable of receiving magnetic resonance signals from a subject and for functioning as a guidewire. To act as a guidewire, in one embodiment the MRI probe is small enough to insert into the guidewire lumen of an interventional device as is known to the art.

In a further embodiment of the current invention, the MRI probe is constructed using materials and designs that optimize mechanical properties for steerability, torque transmission and avoidance of antenna whip failure while maintaining desirable electromagnetic properties in magnetic susceptibly and electrical conductivity.

In a further embodiment of the current invention, the MRI probe's antenna whip is constructed to be flexible and therefore reduce the risk of chamber or vessel perforation.

In a further embodiment, the invention comprises a system, method, or means, whereby a guidewire probe suitable for use in an MRI machine can have multiple interventional tools switched between and guided by the guidewire probe without having to remove the probe from the subject. This is accomplished in one embodiment of the invention by the design and construction of a probe with a practical connection interface between the probe, the tuning/matching circuitry for tuning the antenna whip, and the MRI machine.

In a further embodiment, the invention provides a magnetic resonance antenna assembly no for receiving magnetic resonance signals from a sample and for functioning as a guidewire, comprising a probe shaft including a core of non-magnetic material, a first insulator/dielectric layer for providing insulation, a shielding layer, a second insulator/dielectric layer, and an antenna whip. The core of non-magnetic material may be made of a super-elastic material, such as Nitinol or any other non-magnetic material whether metallic or non-metallic. The non-magnetic core may include a coating of conductive material which could comprise gold, silver, alternating layers of gold and silver or copper or aluminum, for example. A clip-on connector may be further provided for making an electrical connection to a magnetic resonance scanner, the clip-on connector enabling loading and unloading of interventional devices during a procedure without removal of the probe from the subject. The antenna whip may additionally comprise a linear whip, a helical whip, a tapered or a combination whip depending on the desired mechanical and electric properties of the antenna whip.

BRIEF DESCRIPTION OF THE DRAWINGS

Other objects, features, and advantages of the invention will be apparent from the following detailed description of the preferred embodiments as illustrated in the accompanying drawings, in which reference characters refer to the same parts throughout the various views. The drawings are not necessarily to scale, emphasis being placed upon illustrating principles of the invention.

FIG. 18 shows a clip connector of the instant invention. 18A is in unlocked form and 18B is in locked form.

FIGS. 24 and 25 show different views of a connector of the instant invention which use a vice-like connector between the connector portion and the mated connector portion and allow the guidewire to rotate within the connector.

DETAILED DESCRIPTION

Figure 1:
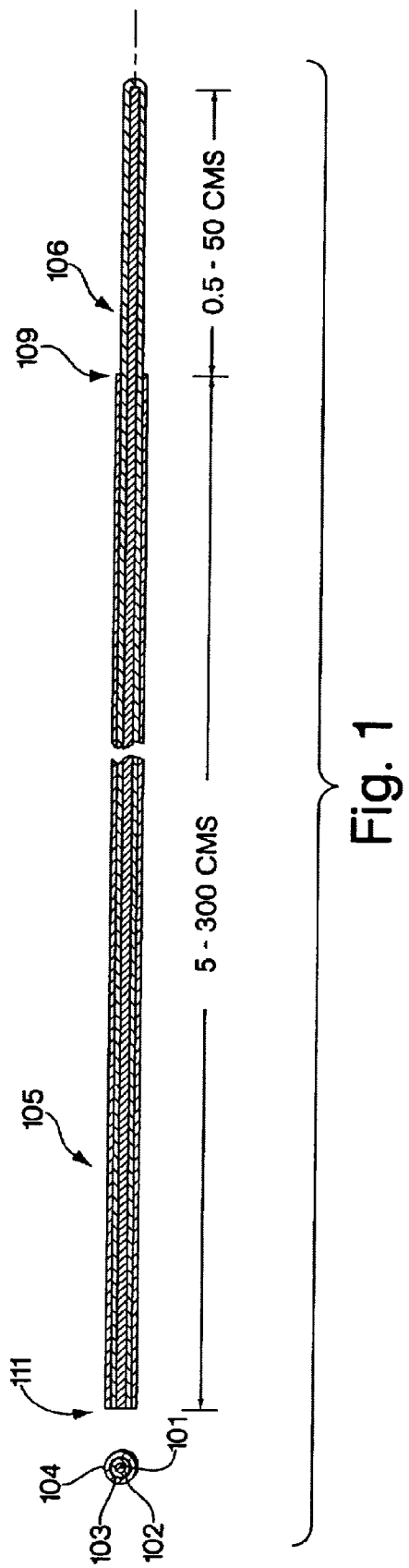
FIG. 1 shows a cross-sectional side and end view illustrating the structure of a guidewire probe with a linear whip antenna according to the invention.

This disclosure will discuss the invention primarily in terms of a loopless whip antenna for use with a guidewire probe that is suitable for vascular procedures on human subjects in a conventional MRI machine designed for medical use. This description does not, however, limit the scope of this invention. In particular, the invention can comprise any type of probe with any type of MRI antenna whether a whip antenna or not and whether of looped, loopless or of other design which is suitable for use as a guidewire as is understood in the art. The invention can also comprise any type of probe or other device for insertion into a subject, whether or not for use as a guidewire, that comprises a helical coil being used as an antenna. This includes, but is not limited to; any type of biopsy device; any type of interventional tool; any type of probe or device which could be used simultaneously to an interventional tool; any type of catheter, known now or later discovered, including, but not limited to, catheters for any use associated with endovascular, urinary, nasogastric, endotrachial, endobilliary, peritoneal, intracranial, intradural, intraarticular, urologic, nasopharyngeal (including endonasal approaches to the cella turcica) procedures; any type of probe, known now or later discovered, including, but not limited to, probes for any use associated with endovascular, urinary, nasogastric, endotrachial, endobilliary, peritoneal, intracranial, intradural, intraarticular, urologic, nasopharyngeal (including endonasal approaches to the cella turcica) procedures; any type of tube including, but not limited to, a jejeunostomy tube, a gastrostomy tube, colostomy tube, or a nephrostomy tube; any other type of intrabiological device; any type of device for use within non-biological matter; or any of the previous in any combination.

The subject of the invention is also not limited to human beings but can be used on any subject where the use of a guidewire is desired. These include but are not limited to, applications of the probe in the body or portion of the body of any human, non-human animal, or other biological organism, living, deceased or otherwise; applications involving placement of the probe in any fluid, gel, solid, gas, plasma or other state of matter where the use of a guidewire is desired in that matter, placing the probe in the vicinity of a portion of a subject for the purpose of viewing that portion of that subject through the probe's proximity, or guiding a device to within that portion's proximity; the use of a probe to simultaneously guide an interventional device and image the area on which the interventional device is to be used; or any of the previous in any combination.

The invention is also not limited to a conventional MRI machine used medically but can be used in any type of scanning device that can measure magnetic resonance. Therefore, we use the term MRI machine to apply to any type of machine, device, system, means, or process which allows the detection of magnetic resonance in any type or state of matter, such device being currently known or later developed, whether for use on humans, non-human animals, other biological organisms, biological tissues or samples, or inorganic matter. Such an MRI machine may be of any shape and for scanning any size subject or portion of a subject.

The application of guidewires is also not limited to vascular interventions. Guidewires are commonly used in many non-vascular applications for the placement of various probes and catheters into the gastrointestinal (GI) tract, the biliary duct, the urethra, bladder, ureter and other orifices, punctures, or surgical openings. Systems according to the present invention may be adapted to a plurality of minimally invasive applications. Guidewires according to the present invention may, in certain embodiments, be used for passage into and through the upper airway, trachea and bronchial tree. Examination of these structures using the systems of the present invention may be performed to detect abnormalities of the lungs or tracheobronchial tree, ideally at an early stage for early treatment. As an example, the early detection of a pre-malignant lesion in the tracheobronchial tree could permit early extirpation before an invasive cancer develops; even if an invasive cancer is detected, it may be possible to detect and treat these lesions at their earliest stages, before lymph node invasion or distant metastasis. Similarly, the systems and methods of the present invention are applicable to any body lumen or body cavity wherein early detection of pre-malignant and malignant disease is desirable. As examples, these systems and methods could be used for the evaluation of the esophagus, stomach and biliary tree to identify neoplasms and to distinguish benign from malignant tissue proliferation. As examples, these systems and methods could be used for the evaluation of the colon and rectum to identify abnormalities and malignancies. These systems and methods could also be used for the evaluation of the male and female urogenital systems, including bladder, urethra, prostate, uterus, cervix and ovary, to identify therein abnormalities and malignancies.

Further, the diagnostic function of the MRI would be useful in the evaluation of any mucosal malignancy to identify how far through the wall of the affected organ the malignancy has invaded. It is understood in the art that extent of invasiveness into and through the wall, diagnosable by MRI, is an important characteristic of an intraluminal cancer.

The diagnostic function of the MRI, as the probe is guided to the target tissue, may be combined with therapeutic interventions. For example, a small lesion found within a body lumen using the systems and methods of the present invention may be suitable for localized ablation, wherein the lesion's response to the delivery of radio frequency energy or other ablative energy can be monitored in near real time by the high resolution MRI as disclosed herein.

The scale of the devices described herein may be dimensionally adaptable to a number of body cavities and lumens traditionally inaccessible to interventive methods known in the prior art. For example, the eustachian tube, the nasal airways and the craniofacial sinuses may all be accessible to a probe designed in accordance with the present disclosure. Using one of these orifices as an entryway into the craniofacial skeleton may permit the diagnosis or evaluation of a variety of otolaryngological and neurological conditions with greater precision than is currently available using whole-patient CT or MRI. As an example, transsphenoid evaluation of intracranial or sellar lesions may be possible. The imaging of these lesions provided by the systems and methods of the present invention may be combined with therapeutic techniques for extirpating or otherwise treating the lesion using minimally invasive technologies. For example, an aneurysm of the Circle of Willis that is identified using high-resolution MRI may be suitable for clipping under MRI guidance using minimally invasive techniques. As another example, a pituitary tumor can be evaluated for its extensiveness using these systems and methods, and its resection can be precisely monitored. Use of these systems and methods may also permit diagnosis of abnormalities in organs considered inaccessible to traditional monitoring methods. For example, the pancreas may be examined, using an embodiment of the present invention, permitting the early diagnosis of pancreatic lesions. As another example, embodiments of the present invention may be adapted for intracranial use, for the diagnosis of lesions of the central nervous system or for precise anatomic delineation thereof. Ablative techniques may be combined with these diagnostic modalities to permit treatment of abnormalities using embodiments of the present invention to help determine the extent of the pathology and to monitor the effectiveness of the ablation in removing the abnormality. Trigeminal neuralgia is an example of a condition where delineation of the relevant intracranial anatomy is vital for the identification of the neuroanatomical structures to be ablated or treated. MRI using the systems and methods of the present invention may usefully help direct the surgeon to the precise tissues requiring treatment.

Conventional minimally invasive techniques such as laparoscopy, thoracoscopy, mediastinoscopy, and arthroscopy may all be combined with these systems and methods to permit more accurate identification of target lesions and to monitor therapies directed at the target lesions. MRI guidance according to these systems and methods may be particularly valuable in determining the extensiveness of a lesion that is to be resected or biopsied. For example, in mediastinoscopy, it may be difficult to distinguish between large blood-filled vessels and pathological lymph nodes, the latter being the target for the biopsy being performed. The operator performing the procedure must sample the pathological lymph nodes without damaging the large vessels in the area, an inadvertancy that can result in profound, even exsanguinating hemorrhage. MRI guidance according to these systems and methods can not only distinguish among the various types of anatomic structures, but also can map out the extent of lymph node involvement and direct the operator towards those lymph nodes most likely to bear the abnormal tissue being sought. A number of applications will be readily apparent to practitioners of ordinary skill in the art, whereby a conventional endoscopy procedure combined with these systems and methods will permit the diagnostic evaluation of a tissue or organ within a body lumen or a body cavity. The intraperitoneal space, for example, may be usefully evaluated using these systems and methods, with access to this space being provided by laparoscopic instrumentation, and with MRI being used to approach and identify target tissues. Intraperitoneal diagnosis using these systems and methods may be helpful in diagnosis of various retroperitoneal lymphadenopathies, such as those indicative of lymphoma, or such as those indicative of spread from a malignant melanoma of the lower extremity. Other examples may be evident to ordinarily skilled practitioners in the medical arts.

Combining these systems and methods with other diagnostic modalities may permit better or earlier diagnosis of malignancies. For example, use of contrast agents in addition to the systems and methods described herein may permit identification of tumors on the basis of their abnormal blood flow or metabolism. Contrast agents or other markers carried by body fluids may permit these systems and methods to be used for diagnosis of abnormal bleeding sites, such as occult gastrointestinal bleeding points or bleeding varices, situations where direct visual inspection of the lesion may have limited diagnostic or therapeutic value.

It is understood that advances in fabrication of static MRI machines will permit more localized anatomic evaluation of specialized body parts, and further will permit easier access to the patient for interventional techniques. These developments may permit the systems and methods of the present invention to be used as a replacement for various ultrasound-guided techniques such as fertility procedures. In certain embodiments, the present invention may be adapted for screening procedures using probes dimensionally adapted for appropriate bodily orifices. For example, these systems and methods may be useful in identifying and determining extensiveness of gynecological cancers, including cervical cancer, uterine cancer and ovarian cancer. Other applications should become available to practitioners of ordinary skill in the art with no more than routine experimentation.

The probe of this invention can be described and understood as having multiple different forms of antenna whip and design. The first of which is depicted in FIG. 1 wherein the probe comprises a linear whip antenna 106.

Figure 2:
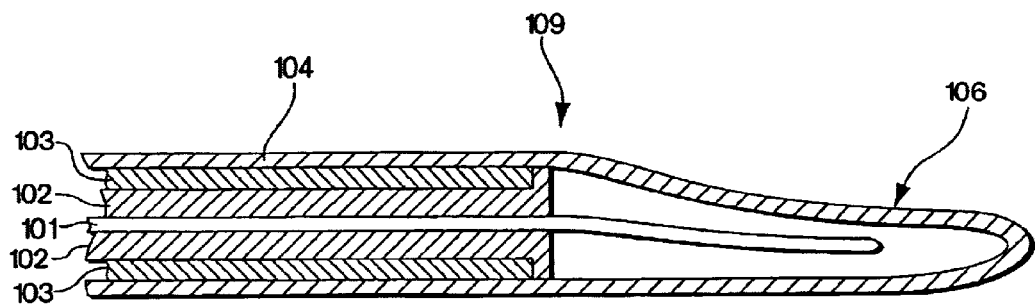
FIG. 2 shows a cross-sectional side view illustrating the structure of one potential shielded linear whip antenna according to the invention.
Figure 3:
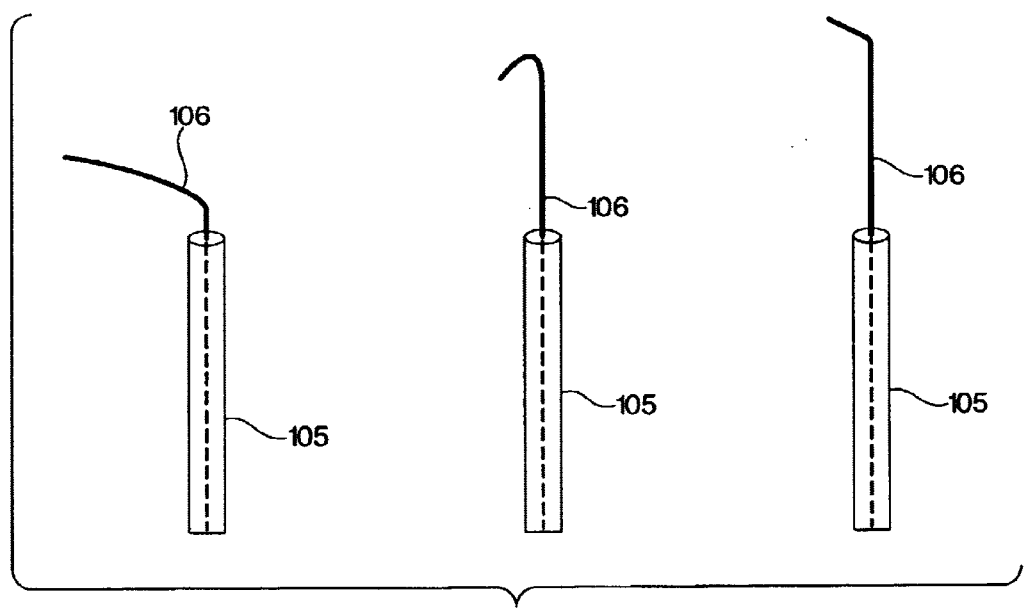
FIG. 3 shows three potential alternate shapes for a linear whip antenna.

The whip refers to the antenna at the end of the probe which is a whip antenna. In this case the whip comprises a primarily unbent protrusion and is therefore called a linear whip antenna 106. The probe preferably comprises a probe shaft 105 with a distal end 109 and a proximate end 111. The probe shaft can be comprised of multiple layers of different materials including a core 101 having at least one first electrically conducting component, a first insulator/dielectric 102 for providing insulation, a shielding 103 having at least one second conducting component, and an optional second insulator/dielectric 104 as shown in FIG. 2. The linear whip antenna 106 extends from the distal end 109 of the probe shaft 105. It would be understood that a linear whip antenna 106 does not have to be straight but may have a curve or slight hook at the end as is understood in the art to facilitate engagement of the device into complex vessels or other openings (such as ducts etc.) as shown in FIG. 3. In one embodiment of the invention, it would be understood that the linear whip antenna 106 would be straight or straight and flexible or could be bent to form other non-linear shapes as the probe was twisted through complicated pathways within the subject. In an alternative embodiment the linear whip antenna can comprise a ribbon or paddle shape such as those shown in FIG. 16.

The core 101 can comprise a super-elastic material such as the Tinol® range of materials (also known as Nitinol or NiTi). Super-elastics generally comprise a titanium-nickel alloy and have many positive attributes for use as a base for the probes of this invention. Super-elastics may be significantly deformed and still return to their original shape. Such deformation and "shape memory" can take place through actions based on changes in temperature. Super-elastic materials are also known for high biocompatibility and show good properties for use within biological organisms or matter. Super-elastics in the antenna designs of this invention could be of any shape including wire, ribbon, microtubing, sheets or any other form as is known to the art but in one embodiment will comprise Nitinol wire that can be plated with layers of gold-silver-gold, or layers of gold, silver, copper, or aluminum applied either singly or in combination. The core 101 can alternatively comprise different materials, including, but not limited to, MR-compatible stainless steel, other metallic materials that are non-magnetic, non-metallic substances such as carbon, glass fiber, or polymer, that can be plated with a layer of a good RF conductor such as copper, silver, gold, or aluminum either singly or in multiple layers, or any of the previous in any combination. In the case of an aluminum core 101, the surface can be readily oxidized as is known to the art to provide the first insulator/dielectric 102.

The first insulator/dielectric 102 and the second insulator/dielectric 104, may comprise any insulator/dielectric as is known to the art including any polymer, such as, but not limited to, an elastomeric grade PEBAX, Nylon, Teflon®, polyurethane, fluoroethylene polymer (FEP), or polyvinylidene fluoride (PVDF), or any combination of polymers with appropriate electrical properties. The insulator/dielectric could also comprise aluminum oxide or any other nonpolymeric element or compound as would be understood by one of skill in the art.

The thickness of the first insulator/dielectric 102 and the second optional insulator/dielectric 104 can be determined so as to control the impedance of the cable formed. The wire can have a uniform impedance throughout the length or the impedance can vary with length, for instance, by having low impedance closer to the proximate end 111 as compared to the distal end 109.

The shielding layer 103 may comprise any MR-compatible conductive material including, but not limited to, copper plated with silver, copper plated with gold, Nitinol plated with gold, conductive inks, conductive coatings or any of the previous in any combination. The shielding can be in the form of a braid, a mesh, or a continuous tubing such as, but not limited to, a gold-silver-gold plated Nitinol hypotube. The shielding can be continuous or coiled toward the distal end 109 and can extend beyond the distal end 109 of the probe shaft 105 or may be discontinued at the distal end 109 of the probe shaft 105. Discontinuing the shielding can create a stronger signal from the antenna, but may create detrimental effects when the probe is used in a human body.

Figure 4:
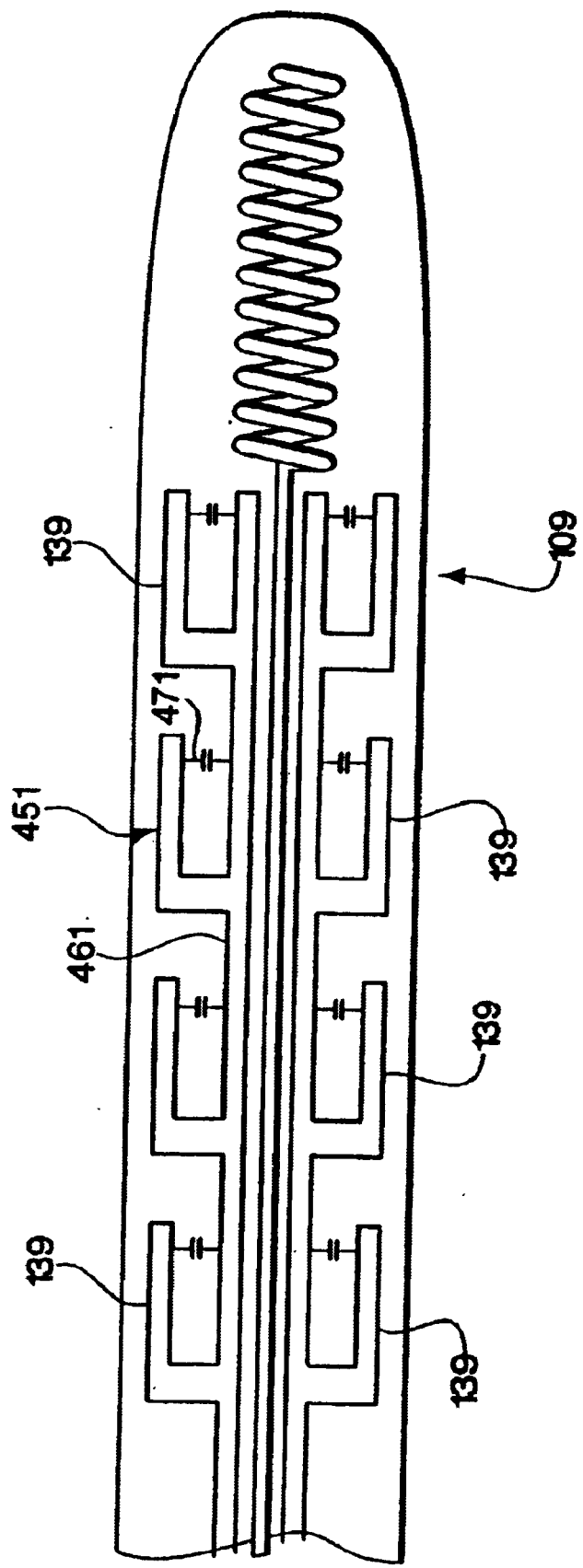
FIG. 4 shows a potential embodiment of the invention wherein the shielding comprises a series of balun circuits.

To increase the safety and the signal-to-noise ratio of the antenna, the shielding 103 can be added to the probe shaft in the form of a balun circuit as is understood in the art. This reduces the effect of induced currents due to external RF and magnetic fields. The tertiary shielding 451 can be continuous or discontinuous. It can have capacitors connecting the discontinuous sections or it can be connected directly to the primary shielding 461 or connected to the primary shielding 461 with capacitors 471 or by any other method understood in the art, or by a series of balun circuits 139 as shown in FIG. 4.

In another embodiment of the present invention, a balun circuit is placed on the probe in a tuned form (also known as a bazooka circuit) as is known to the art. This tuned balun circuit could help to increase the SNR performance and reduce the induced currents on the wire during an RF pulse transmission by any external RF coil (such as the transverse magnetic field in an MRI machine). This circuit may also decrease the risk of possible excessive Ohmic heating from the presence of the probe inside the body.

The second optional insulator/dielectric 104 is desirable over the antenna whip as depicted in FIG. 2 so as not to insert a straight cylindrical segment of bare wire into the patient with direct blood and tissue contact. The problem with this solution, however, is that the optimal length of the whip portion of the device is determined based upon the operating electromagnetic wavelength in vivo which in turn depend upon the effective dielectric constant as experienced by the antenna. For the case of a bare wire loaded in water, this length is approximately 4–12 cm, which represents a reasonable length for in vivo use. The addition of a second insulator/dielectric 104 to the outer surface of the antenna however, decreases the effective dielectric constant, which in turn increases the operating wavelength and thus increases the optimal whip length from 4–12 cm. It is clear that a significantly longer antenna whip may be unsuitable for some in vivo use, an alternative insulated whip design could be desired when the antenna is insulated as is discussed below. In addition, covering the antenna with a second insulator/dielectric 104 increases the diameter of the antenna making it increasingly difficult to insert in small vessels. In one embodiment, the linear whip antenna 106 has the narrowest possible diameter to allow such insertion.

A typical assembly procedure for an MRI probe of the present invention can involve the following steps. First, the first insulator/dielectric 102 is attached to a gold-silver-gold plated Nitinol core 101. This can be done by means of extrusion, drawing, a heat shrink tubing, or any other method known to the art. Next, the shielding 103 is loaded on the assembly leaving a portion of the assembly exposed to act as the linear whip antenna 106. This can be done by means of braiding, plating, painting, sputtering, or any other means known to the art. Alternatively, a metallic hypotube can be used instead of braiding to add mechanical stiffness to the probe shaft. Lastly, the second insulator/dielectric 104 is loaded on the probe shaft 105. A connector can then be attached to the proximate end 111 of the probe shaft 105 to facilitate connecting to the interface circuitry to be connected to the MRI scanner. The connector can be any type as is known to the art, or could alternatively be any of the connectors described below. In a further embodiment of the invention, the connector can be replaced by mechanical forming of the proximal tip to enable attachment of a snap-fit connector or by any other means of connections or termination of the probe as would be known to one of skill in the art. An optional coating of lubricant may further be added to the probe shaft 105 and/or antenna whip to reduce drag.

It is covered in this invention to manufacture the linear whip antenna 106 and probe shaft 105 as a single piece as is described above. Alternatively, the probe shaft 105 and linear whip antenna 106 could be constructed as two separate pieces and attached together by any means known to the art either permanently (including, but not limited to, use of high temperature or cold impact welding, soldering and/or electrically conducting glue or epoxy) or removeably (including, but not limited to, a snap-on or locking connection).

Figure 5:
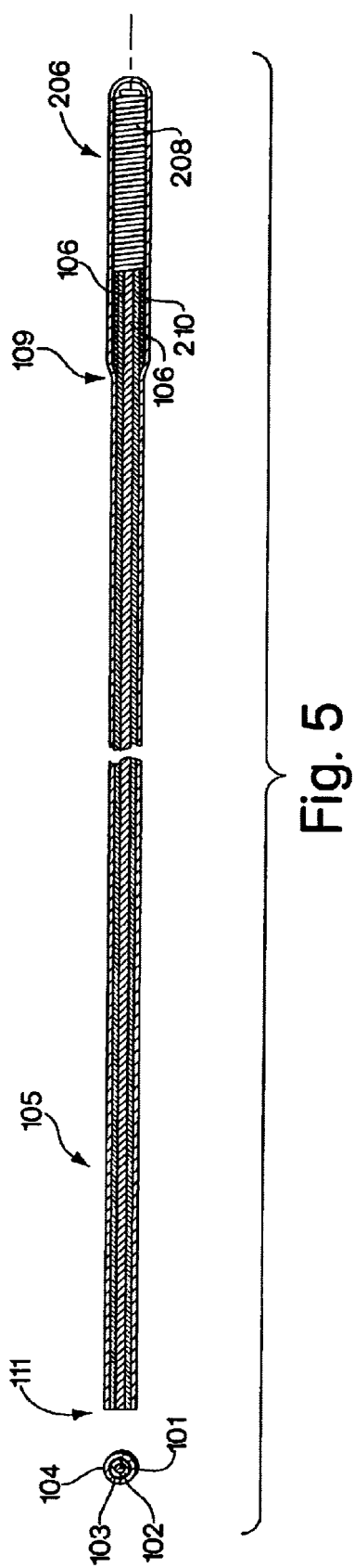
FIG. 5 shows a cross-sectional side and end view illustrating a guidewire probe according to an embodiment of the invention wherein the antenna whip comprises a combination whip where a helical coil is connected to a linear whip antenna at multiple points.
Figure 6:
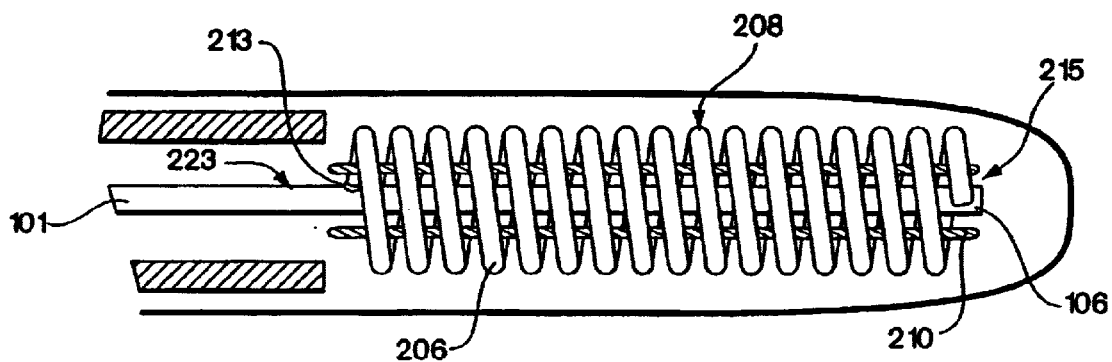
FIG. 6 shows a potential guidewire probe with a helical coil electronically connected to a linear whip antenna at a single point.
Figure 7:
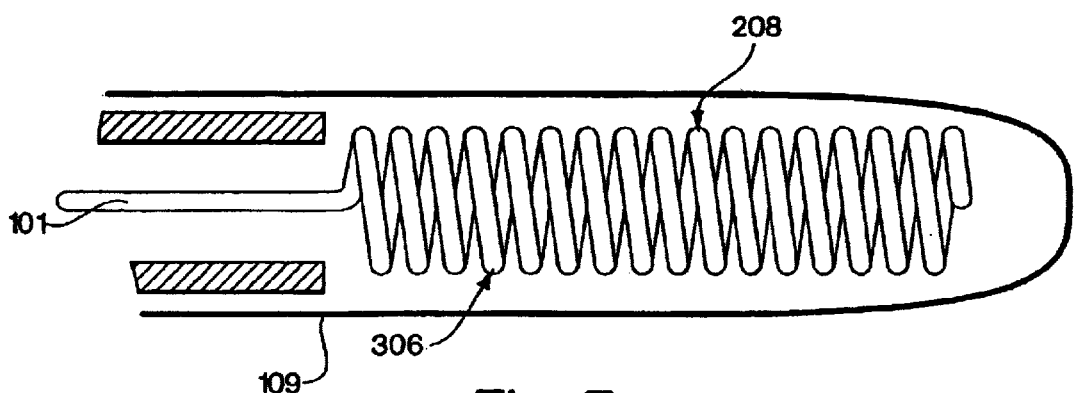
FIG. 7 shows a potential guidewire probe where a helical coil alone comprises a helical whip antenna.
Figure 9:
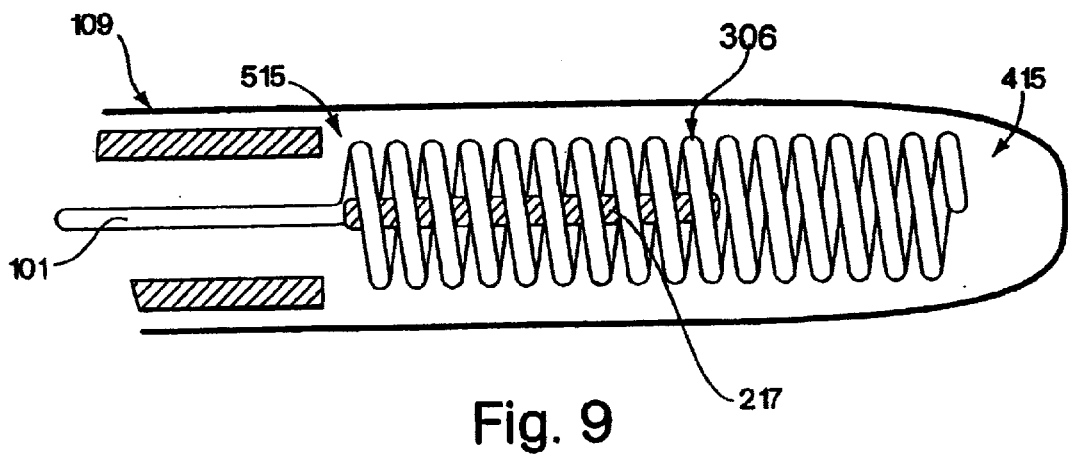
FIG. 9 shows a potential guidewire probe where a core is present inside a helical whip antenna.

FIGS. 5, 6, 7, and 9 show alternative embodiments of the invention using a helical coil antenna that obtains through its shape the ability to be the same physical length as a linear whip antenna, while still maintaining the electrical length of a much longer linear whip and therefore having desirable properties even when shielded by a second insulator/dielectric 104. FIGS. 5 and 6 show a combination whip antenna 206 where a helical coil is placed over and electrically joined to a linear whip antenna 101. FIG. 7 shows a guidewire probe with a helical coil whip antenna 306 where the helical coil 208 comprises the antenna alone. FIG. 9 shows a variation on the helical coil whip antenna 306 of FIG. 7 that contains a core 217 inside at least some of the coils of the helical coil 208. The core 217 can provide modification to the flexibility of the helical coil whip antenna 306 for insertion into, or navigation inside, a subject. The core 217 can be of non-conducting material including, but not limited to, a polymer, or can be an electrically conducting material. The core 217 will usually be non-magnetic. replace the paragraph beginning at page 22, line 13, with the following paragraph:

Helically coiling the antenna shortens the physical antenna length while still producing optimum performance. Covering the antenna with an insulator, usually requires increasing the antenna length to obtain optimum performance because the insulator affects the ability of the antenna to detect signal. In this case, coiling the antenna can be used to compensate for this increase in antenna length. That is, a coil of wire can contain a longer piece of wire in a shorter physical form.

Figure 8:
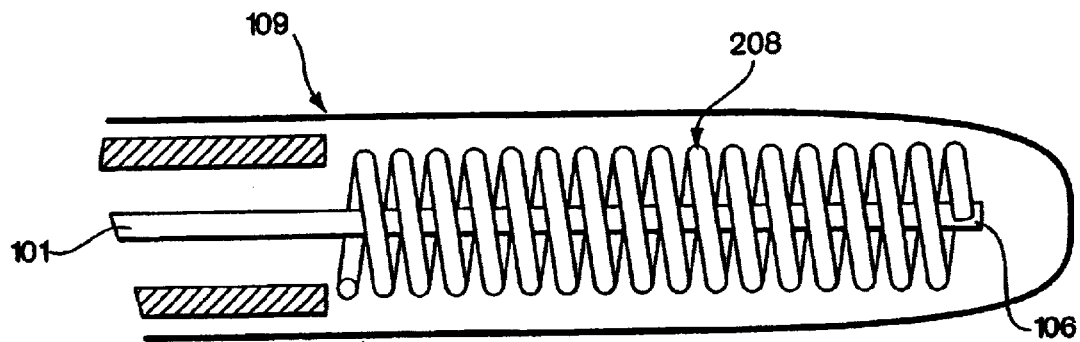
FIG. 8 shows a potential guidewire probe where a helical coil is placed over a linear whip antenna without making an electrical connection between the two.

A helical coil antenna has further mechanical advantages over a linear antenna. In particular, a coil is flexible and "springy" allowing it to navigate through complicated biological pathways without bending, kinking, or breaking, as opposed to a linear antenna which can have many of these problems since it is narrow and may have poor mechanical properties. Therefore, in one embodiment of this invention the helical coil is placed over a linear antenna, not necessarily to change signal, but to "superimpose" preferred mechanical properties on the linear antenna as exemplified in FIG. 8.

The helical coil also provides for detection of magnetic resonance in multiple directions. The signal received by a linear antenna is dependent upon the orientation of the antenna with respect to the main magnetic field as is known to the art. When a linear antenna design becomes bent or changes geometric planes, the sensitivity of the antenna and thus image quality can be degraded, with zero signal detected in some cases.

As diagnostic and therapeutic catheter interventions inherently involve movement of the catheter in planes transverse to the main longitudinal axis of the body, and therefore transverse to the so magnetic fields in the MRI machine, an antenna design capable of removing this orientation dependency would be desirable in many cases. The unique physical geometry of the helical coil antenna allows detection of radio frequencies from two orthogonal components of the processing transverse magnetization, which is known as quadrature detection. Quadrature designs are able to create a circularly polarized electric field that results in a 50% reduction in RF power deposition and up to a 40% increase in signal to noise ratio. In addition to these very important advantages, such a design allows the imaging capabilities of the device to be independent of spatial orientation and therefore it can be used in any vessel or other area in the body.

Figure 10A:
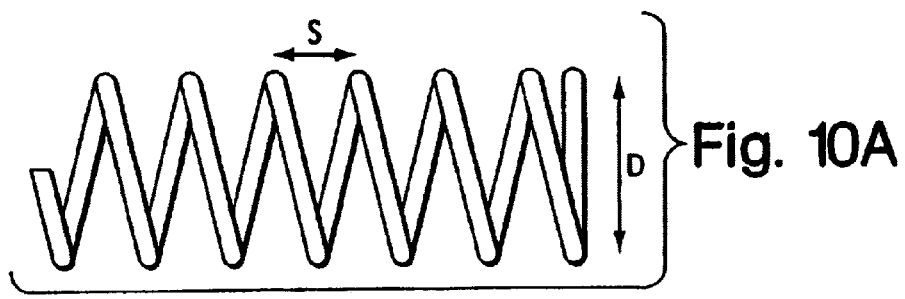
FIG. 10 shows a representation of the receiving properties of a helical coil antenna.
Figure 10B:
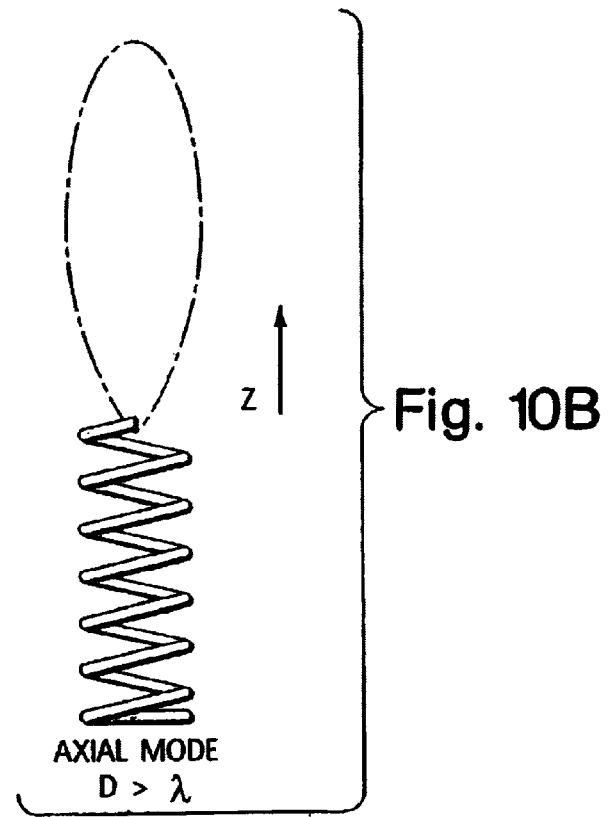
Figure 10C:
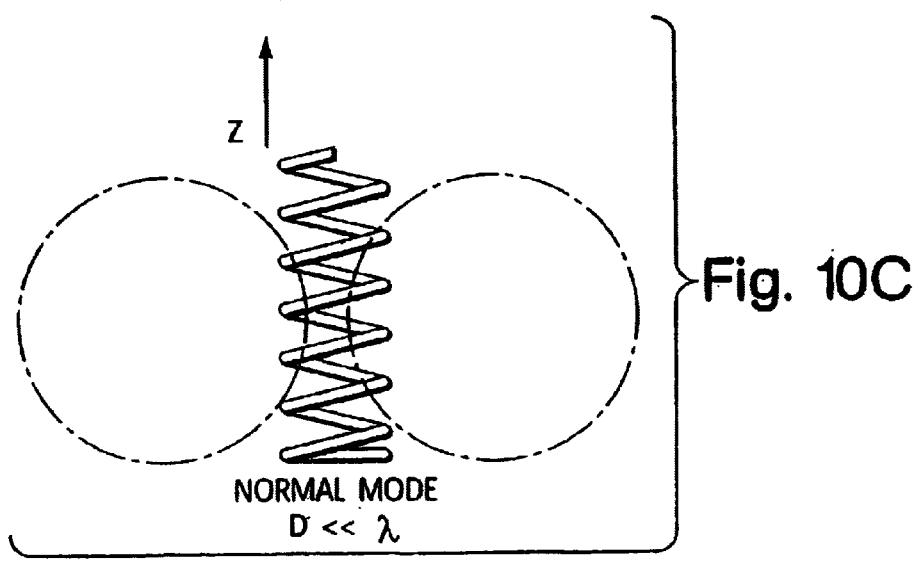

Helical coil antennas have two distinct and very different operating modes depending upon, as shown in FIG. 10, the physical dimensions of the windings and speed of wave propagation through the medium. When the diameter(D) and spacing(S) between the windings is comparable to the wavelength of the RF MRI signal to be detected with the coil inserted in the subject, (D$\lambda$=S$\lambda$=1, where D$\lambda$=helix diameter, S$\lambda$=coil spacing), the helical coil antenna operates in an end fire or axial mode, where polarization occurs primarily along the axis of the helix as depicted in FIG. 10(*b*). This is similar to the operation of the linear antenna. When D$\lambda$ and S$\lambda$ are much smaller than , the helical antenna is said to operate in normal mode where polarization occurs orthogonal or broadside to the helical axis as shown in FIG. 10(*c*) and described in equation (1). Since the RF frequencies used in MRI tend to be very long, normal mode operation is the standard for a probe of the present invention.

FIGS. 5 and 6 show a probe with a helical coil 208 on top of a linear whip antenna 106. This creates a combination whip antenna 206. In one embodiment of the present invention, there can be an electrical connection between the linear whip and the helical coil in one point 213 as shown in FIG. 6 or multiple points. Alternatively, the connection point could be at the distal end 215 of the linear whip antenna 106 instead of at the proximate end 223 as shown in FIG. 6. This allows for both portions to act as antennas and can produce an antenna with higher SNR without increasing physical size significantly. A thin insulator 210 may be placed between the linear whip antenna 106 and the helical coil 208 in any combination antenna 206. In another embodiment of the present invention (FIG. 8), the helical coil 208 and the linear whip antenna 106 are not electrically connected to each other. In this embodiment, the helical coil 208 provides beneficial mechanical properties to the linear whip antenna 106. In particular, it can make the linear-whip antenna 106 more rugged and more flexible allowing for better mechanical properties within the subject. In FIGS. 5, 6 ,7, 8, and 9 the probe shaft 105 can be built similarly to the probe shaft of FIG. 1 and all listed materials for the probe of FIG. 1 are also available for the probes of FIGS. 5, 6, 7, 8, and 9. This type of construction is not limited to these figures. Any probe shaft 105 in any embodiment herein described may be constructed in a similar manner. In assembly, the helical coil 208 will generally be added to a preconstructed probe with a linear whip antenna 106. The addition can either complete the electrical connection to the helical coil 208 or not depending on the desired final probe. Alternatively the probe can be manufactured with the helical coil 208 already attached to the probe in any configuration.

In FIG. 7, the helical coil 208 comprises the entire helical coil whip antenna 306. In this depiction the helical coil 208 is electrically connected to the core 101 of the probe shaft 105. In this case, there is no linear whip antenna 106. Therefore, in another embodiment of the present invention, the whip is entirely helically coiled. This configuration can provide advantages in mechanical properties. In particular, the helical coil whip antenna 306 can be physically shorter or narrower than the combination whip antennas 206 depicted in FIGS. 5, 6, and 8 without significant loss of electrical length. In addition, since the helical coil whip antenna 306 has no linear portions and is only coiled, it is more flexible than any of the other antennas allowing it to turn sharper corners in the subject. Finally, the helical coil whip antenna 306 is more deformable than any of the previous antenna designs which makes the antenna less likely to puncture vessel walls. If desired, the flexibility of this antenna can be adjusted by including a core component 217 attached to the distal end 109 of the probe shaft 105 if nonconducting or unattached if conducting, as shown in FIG. 9. Core 217 need not extend to the distal end 415 of the helical coil whip antenna 306.

Figure 11:
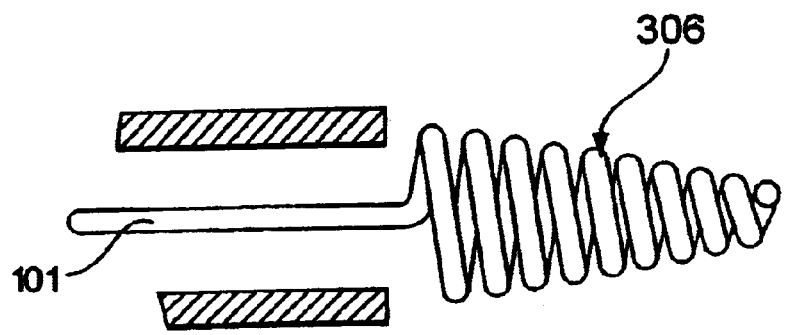
FIG. 11 shows a potential embodiment of a helical whip antenna where the diameter of the coils decreases from the proximate to the distal end of the helical whip antenna.
Figure 12:
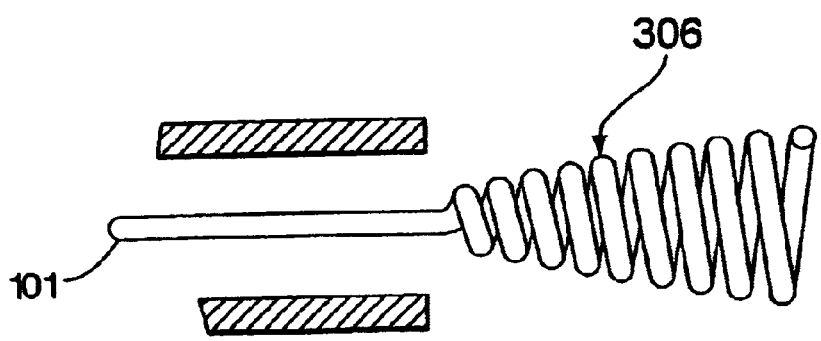
FIG. 12 shows a potential embodiment of a helical whip antenna where the diameter of the coils increases from the proximate to the distal end of the helical whip antenna.
Figure 13:
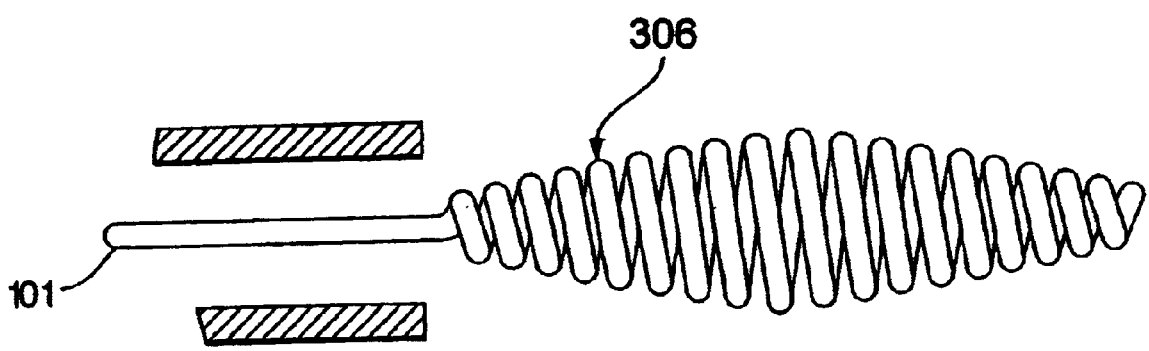
FIG. 13 shows a potential embodiment of a helical whip antenna where the diameter of the coils varies along the length of the helical coil antenna.
Figure 14:
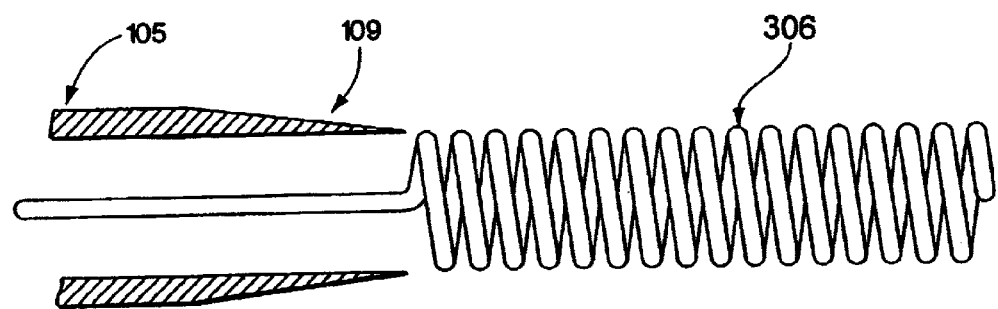
FIG. 14 shows one potential guidewire probe of the instant invention where the probe shaft decreases in diameter at its distal end.

FIGS. 11, 12 and 13 depict alternative embodiments of the helical coil whip antenna 306 that can be used in place of the whip designs shown in FIGS. 7 and 9. In FIG. 11, the helical coil whip antenna 306 has been tapered with decreasing diameter towards the distal end 415 to vary the flexibility of the whip such that it is more flexible at the tip to negotiate blood vessels and the like. In FIG. 12, the helical coil whip antenna 306 is tapered on the proximal end 515 to stiffen the flexibility at the distal end 415. In FIG. 13, the helical whip antenna 306 is tapered at both ends. The taper can be adjusted to provide the desired flexibility gradient. The taper can also repeat at regular intervals (either smoothly or at a sudden transition) or coils of different diameters can be placed anywhere within the length of the helical coil whip antenna 306. Alternatively, the distal end 109 of the probe shaft 105 can be tapered to improve the transition between the probe shaft 105 and any type of whip antenna (a helical coil whip antenna 306 is shown) as shown in FIG. 14.

Figure 28:
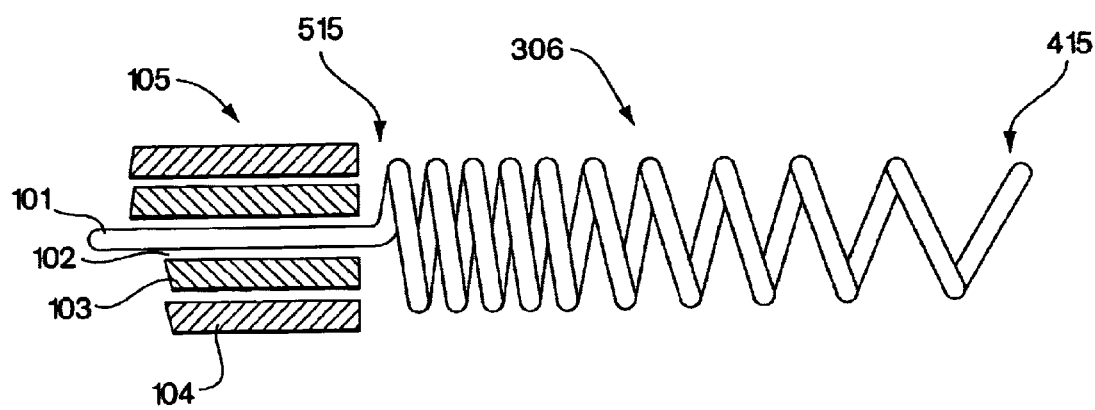
FIG. 28 shows a potential embodiment of a helical whip antenna where the spacing between the coils varies along the length of the helical coil antenna.

In addition to altering the diameter of the coils in the helical coil whip antenna 306, the spacing between the coils can also be modified. As shown in FIG. 28 the spacing of the coils can be closer together at the proximate end 515 and further apart at the distal end 415. This arrangement may allow the construction of a helical coil whip antenna that has greater electrical length but preserves the desired mechanical properties present in a looser packed coil. Alternatively to FIG. 28, the coil spacing could be altered so that the spacing is tighter at the distal end 415 than the proximate end 515, the coil spacing could follow any type of regular change from tighter to looser coils along its length, or the coil spacing could contain coils of random spacing.

The modifications to the diameter and spacing of the coils described above are not limited to helical coil whip antennas 306, but could be used with any of the helical coils 208 described above in order to gain mechanical benefits from such a coil design.

In all of the variations of the designs, the optimum coil length may be preferably calculated or measured as the length that minimizes the real component of the impedance of the antenna as the impedance of the antenna is measured at the point where the shield ends. This length is usually around 0.25 or less times the electromagnetic wavelength of the RF MRI signal in the medium, but other lengths could be used as would be understood by one of skill in the art.

Figure 15:
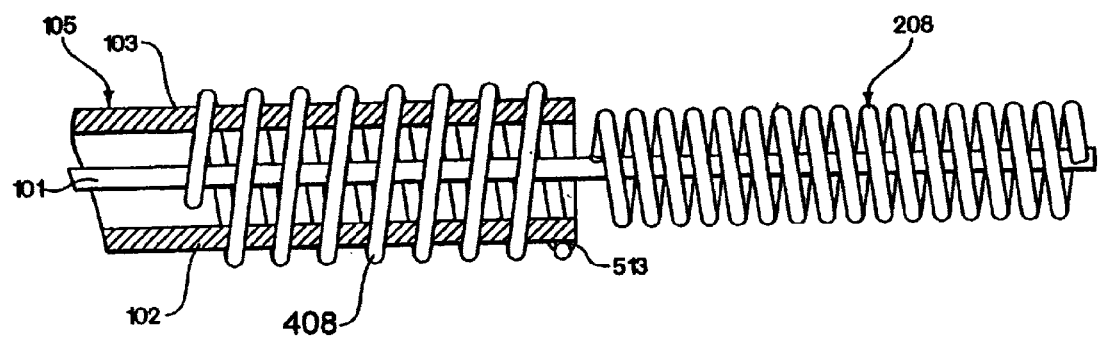
FIG. 15 shows an embodiment of the invention where a second helical coil is placed around the probe shaft and connected to the shielding.
Figure 16A:
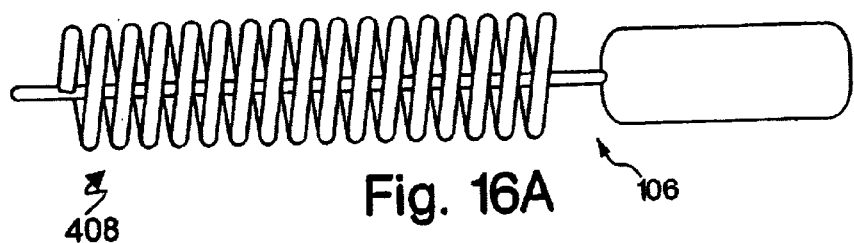
FIG. 16 show embodiments of the invention where a second helical coils is used as shielding around various whip antennas of the invention.
Figure 16B:
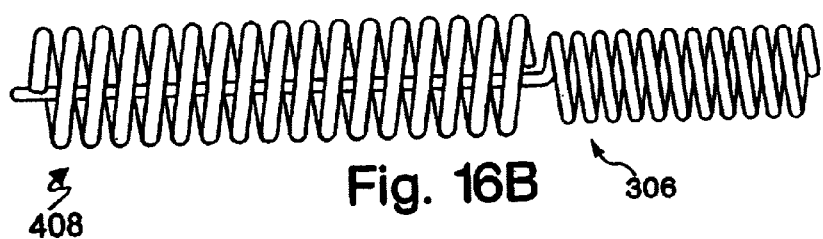
Figure 16C:
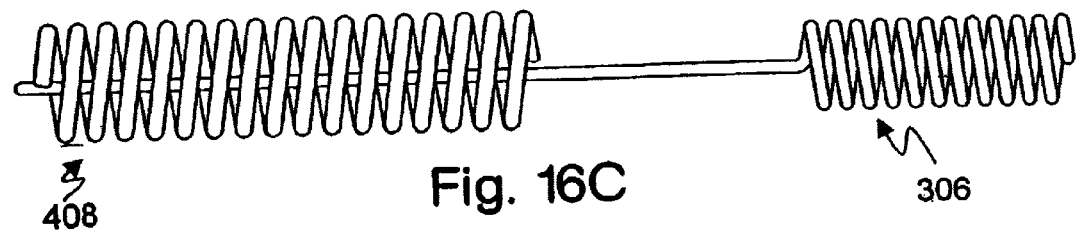
Figure 16D:
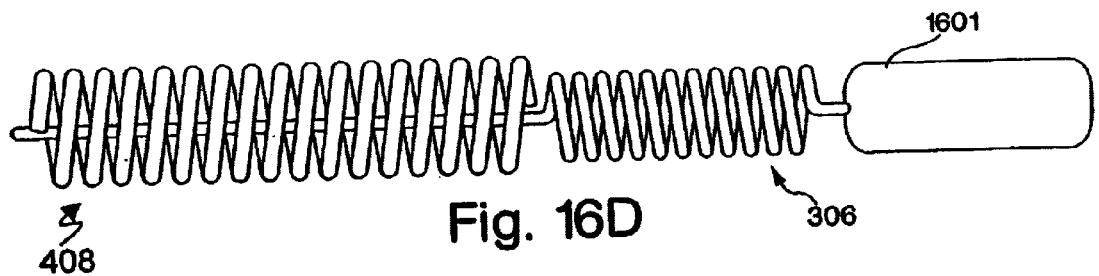

FIG. 15 shows yet another embodiment of the present invention, a second helical coil 408 is connected to the shielding 103 at point 513 of the probe shaft 105 to concentrate the MRI signal sensitivity to a narrow range. The second helical coil 408 can also be connected to multiple points for multiple different electrical properties as would be understood by one of skill in the art. In further alternative embodiments, the shield 103 is completely or partially replaced by the second helical coil 408 which extends for the length of the shaft, insulated from the core 101 by dielectric 102. These arrangements can be used with any type of whip antenna including, but not limited to, those shown in FIG. 16. In particular, a linear whip antenna 106 as shown in FIG. 16A and 16E, a helical coil whip antenna 306 with a separation between the outer shield and whip as shown in FIG. 16B, a helical coil whip antenna 306 without a separation between the outer shield and whip as shown in FIG. 16C or an alternate combination whip with a linear extension 1601 attached to a helical coil whip antenna 306 as shown in FIG. 16D, as well as with any of the other antenna whip designs and herein disclosed or otherwise known to one of skill in the art.

Figure 16E:
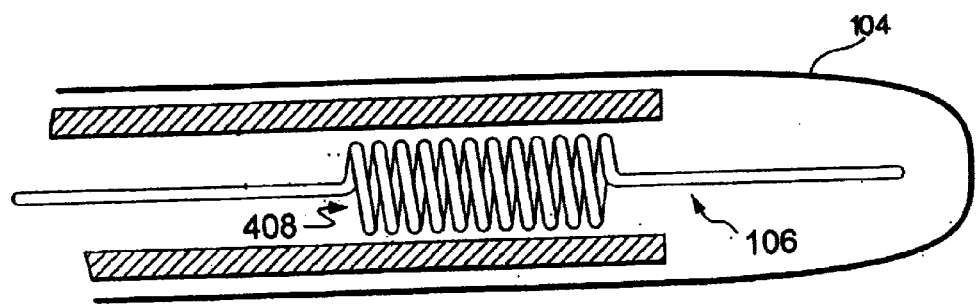

In further embodiments of the invention the second insulator/dielectric 104 is extended over the second helical coil 408 so as to provide protection to the subject from the antenna's interaction with exposed body fluids, tissues, or other portions of the subject as is depicted in FIG. 16E. The second helical coil 408 can also have any alterations of the coil's diameter or spacing along the second helical coil's 408 length as have been previously discussed with regards to the helical coil whip antenna 306.

The connection between this electronic circuit and the probe is a further portion of the invention because a standard RF BNC connector as is known to the art is not well suited for frequent connection and disconnection. In many current procedures where an MRI guidewire would be desired, the tools used as part of those procedures must be changeable without having to remove the guidewire from the subject. In one of the embodiments of the present invention, a connector is used to make an electrical connection between the probe and a tuning/matching and decoupling circuit or interface box of the present invention. This connector connects the interface to the antenna and can be removed and reinstalled as required during an interventional procedure to load and unload other interventional devices. FIGS. 17 through 25 show some examples of connectors of the present invention which are discussed in detail below.

Figure 26:
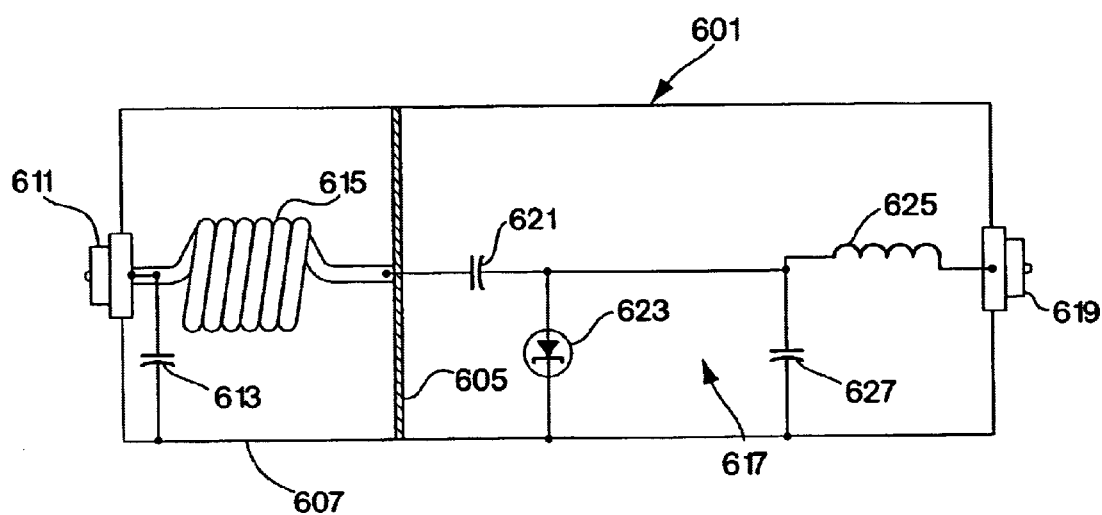
FIG. 26 shows a potential design of an interface box of the instant invention.

FIG. 26 shows one embodiment of an interface box for use between the MRI machine and the guidewire of the instant invention. One embodiment of the interface box consists of a shielded box 601 with two compartments 607 and 617, separated by a partition 605. In one embodiment, all components are non-magnetic. The probe attaches to coaxial connector 611 or another mating connector portion designed to attach to the connector portion of the probe. Coaxial connector 611 can be insulated from the interface box 601. The balancing of the dipole 611 is accomplished by capacitor 613 and coil 615. Coil 615 in one embodiment is a short length (5–10 cm) of 1 mm diameter solid-shield, 50 ohm coaxial cable, which is wound into a coil, increasing the inductance of both the center conductor as well as the shield. For the balancing function, it can be important to present a high impedance to current flow in the shielding 103 of the probe near the interface box 601. This high impedance is accomplished by tuning the LC circuit formed by capacitor 613 and the inductance of the shield of coil 615. In practice, capacitor 613 is selected such that the impedance of the network comprising capacitor 613 and coil 615 matches the impedance of the shielding 103 of the probe. The shield portion of the coaxial cable that forms coil 615 can be electrically connected to the partition 605 of the interface box 601 as shown in FIG. 26.

The center conductor of the coaxial cable that forms the coil 615 feeds through the partition 605 in the interface box 601. The inductance of the center conductor of the coil 615, and capacitor 613, form a tuned circuit that can decouple the probe from the imaging pulses of the MRI machine connected at a coaxial connector 619 (these imaging pulses usually occur at 63.9 MHz). Capacitor 621 can be tuned to maximize probe impedance when PIN diode 623 is turned on during imaging pulses. PIN diode 623 is turned on by a DC level being applied to coaxial connector 619 by the MRI scanner during MRI pulse transmission.

The probe can be tuned to match the generally 10 to 80 Ohm impedance of the MRI scanner amplifier by the network of inductor 625 and capacitor 627. This tuning can be accomplished by connecting a network analyzer to coaxial connector 617 and varying the value of the capacitor 627 until the measured impedance is the desired impedance at based on the frequency of the imaging pulses (usually 63.9 MHz). These numerical values are given as examples and in no way limit the choice of values that could be chosen in use of the invention.

The end of the guidewire antenna can contain a connector portion that allows radio frequency signals to propagate from the scanner to the guidewire antenna and vice versa by connecting the connector portion to a mated connector portion. This connector can be a standard BNC connector or one of the special miniaturized connectors shown in FIGS. 17 through 25. The connectors allow for direct insertion of the guidewire into interventional devices such as balloon angioplasty catheter, stent placement devices. For this to be possible, the connector diameter should be no larger than guidewire probe diameter. Standard connector sizes, however, are often larger than the probe diameter and therefore do not allow for rapid exchanging of interventional devices over the guidewire probe. To overcome this difficulty, we show eight different connector configurations. Although many other designs are possible, the most important feature of these designs are that the diameter of the connector portion on the guidewire probe is not significantly larger than the diameter of the guidewire probe.

The connectors shown in FIGS. 17 through 20, 24, and 25 enable direct electrical contact between the conductors (shield and inner conductor of core) whereas the connectors shown in FIGS. 19–23 have no direct electrical contact.

Figure 17A:
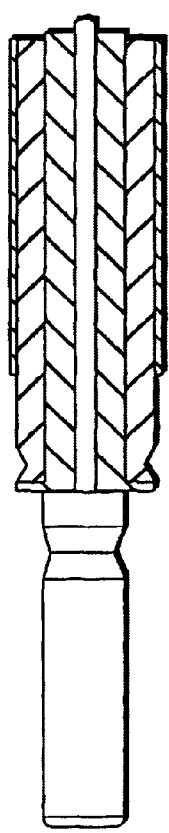
FIG. 17 shows a potential snap-on connector of the instant invention. 17A shows the male connector portion and 17B shows the female connector portion.
Figure 17B:
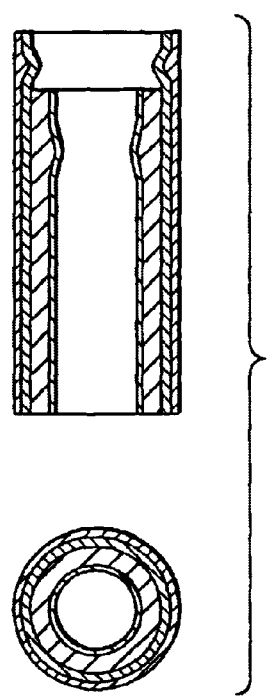

FIG. 17 shows a snap-on connector. The connector at FIG. 17A is the male connector portion. Its diameter is smaller or the same size as the diameter of the guidewire probe. FIG. 17B is the female mated connector portion. They are connected to each other with a small amount of pressure in the direction along the length of the connector and removed easily by pulling the connectors apart.

Figure 25:
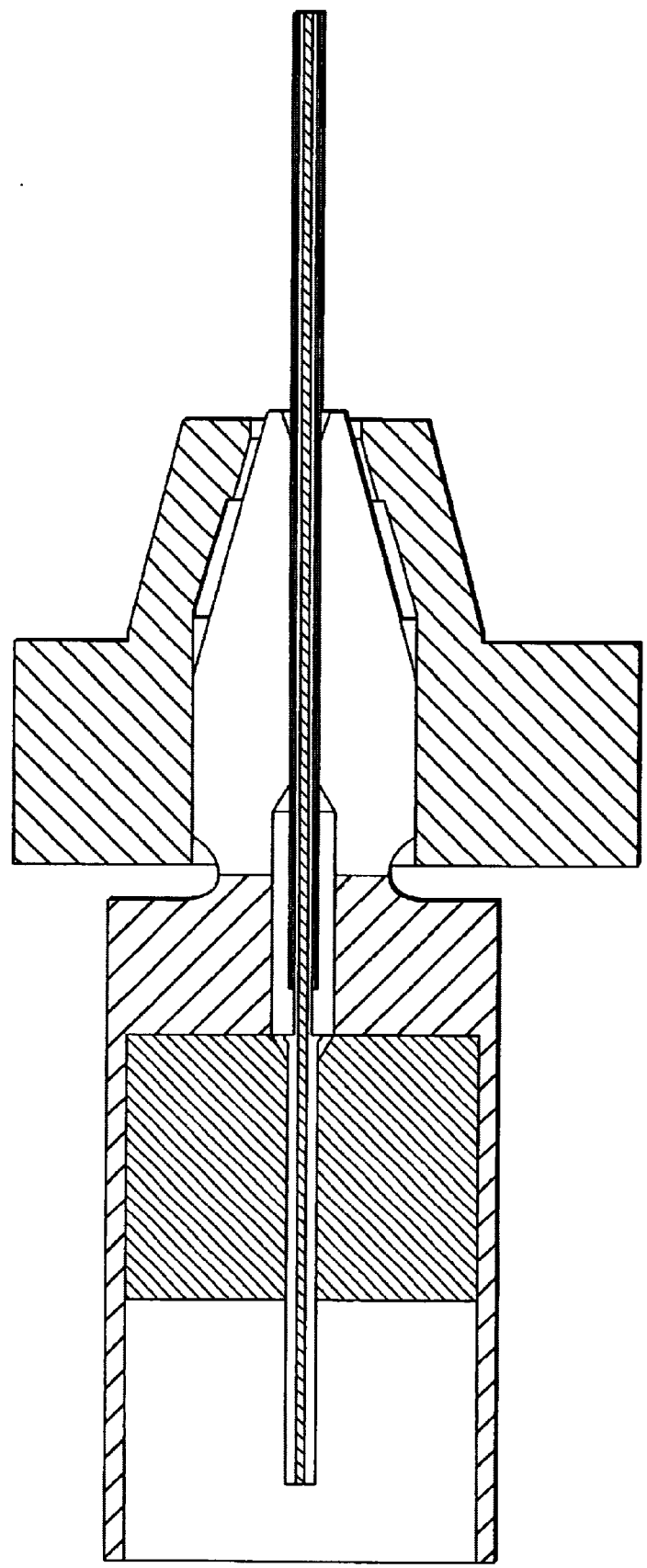

FIG. 18 shows a clip connector. The male connector portion's 1002 diameter is not larger than the diameter of the guidewire probe. With a clip lock mechanism, 1006, the female mated connector portion 1003 is connected to the male connector portion 1002. The mechanism shown by FIG. 18 enables free rotation of the connector. This enables the user to freely rotate the guidewire while it is connected. 1004 shows a coaxial cable connecting the interface box 1005 to the mated connector portion. FIGS. 24 and 25 show an alternative design of this type of connector wherein a vice-like connection is employed instead of the clip. Again this design allows for the guidewire to rotate freely while it is connected.

Figure 19:
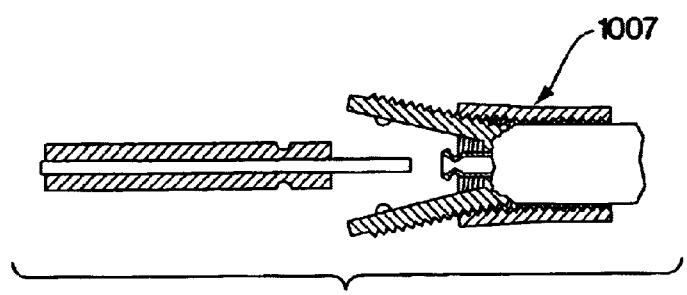
FIG. 19 shows a screw-lock connector of the instant invention.

FIG. 19 has the screw 1007 on the female mated connector portion that is an alternative to the clip lock mechanism, 1006 shown in FIG. 18.

Figure 20A:
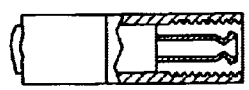
FIG. 20 shows a screw style connector of the instant invention. 20A shows the female portion and 20B shows the male portion.
Figure 20B:
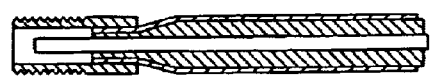

FIG. 20 shows another type of screw connector. FIG. 20A is the female connector portion that is a part of the guidewire probe. The male mated connector portion shown in FIG. 20B can be connected to a coaxial cable that leads to the interface box.

One problem with the connectors shown in FIGS. 17 through 20 is difficulty in using in a wet environment. When the connectors are wet or have blood or other body fluids on them, their performance may degrade. Therefore, a connector was designed that can be used in wet environment. The connectors shown in FIGS. 21–23 do not require direct electrical contact between the two connector portions.

Figure 21:
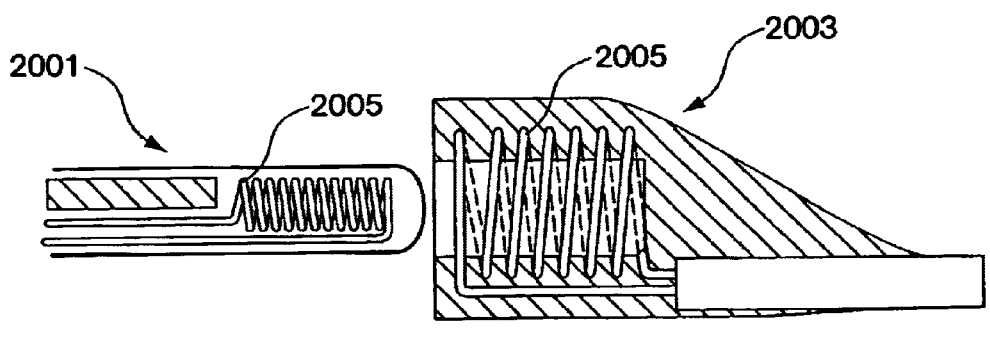
FIGS. 21–23 show alternate connectors whereby there is no direct electric contact between the male and female members of the connector.

FIG. 21 shows a solenoidal coil 2005 inside both female and male connectors portions. The male connector portion snaps in the female mated connector portion 2003 but the electrical wires are not touching each other. The signal is transmitted from one to the other by the coupling of electromagnetic waves.

Figure 22:
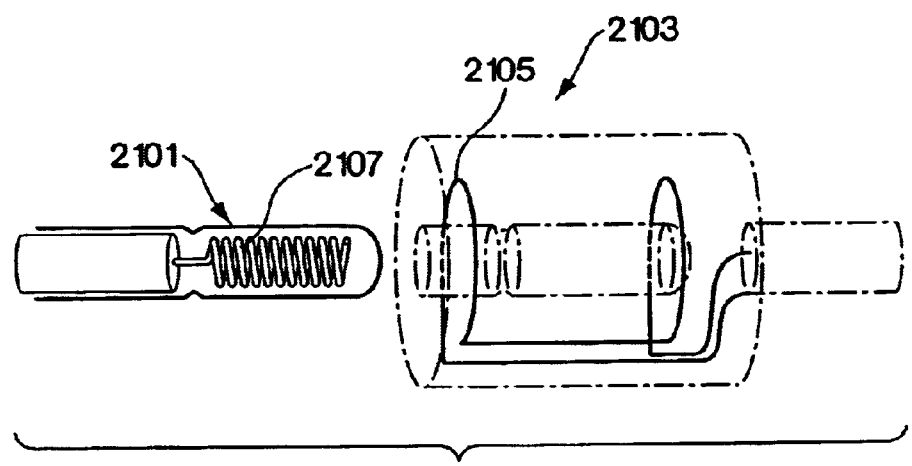

FIG. 22 shows a coaxial cable with extended inner conductor 2105 as the mated connector portion 2103 and an opposed solenoidal coil 2107 as the connector portion 2101 on the guidewire probe.

Figure 23:
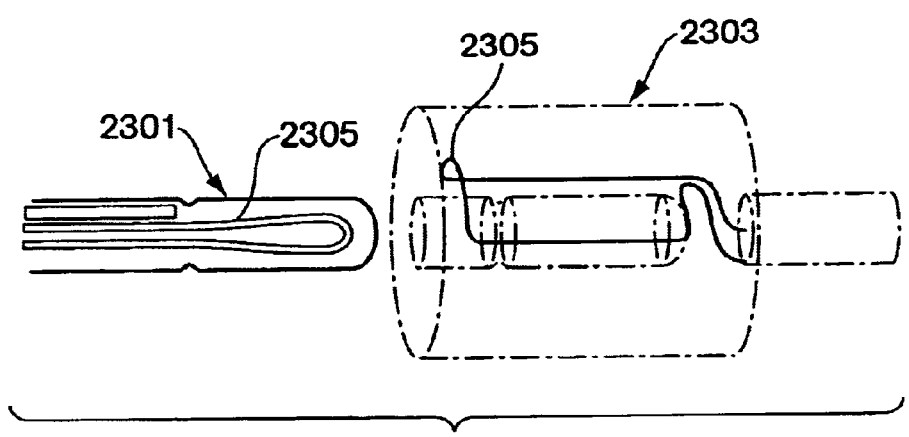

FIG. 23 shows a loop coil 2305 in both ends of the connector. As in the other, the male connector portion 2301 snaps on the female mated connector portion 2303. The electromagnetic waves are transmitted from one coil to the other enabling connection.

One further advantage of using these connectors (FIGS. 21–23) are the isolation of the circuits. Any direct current from one connector will not appear on the other.

Figure 27:
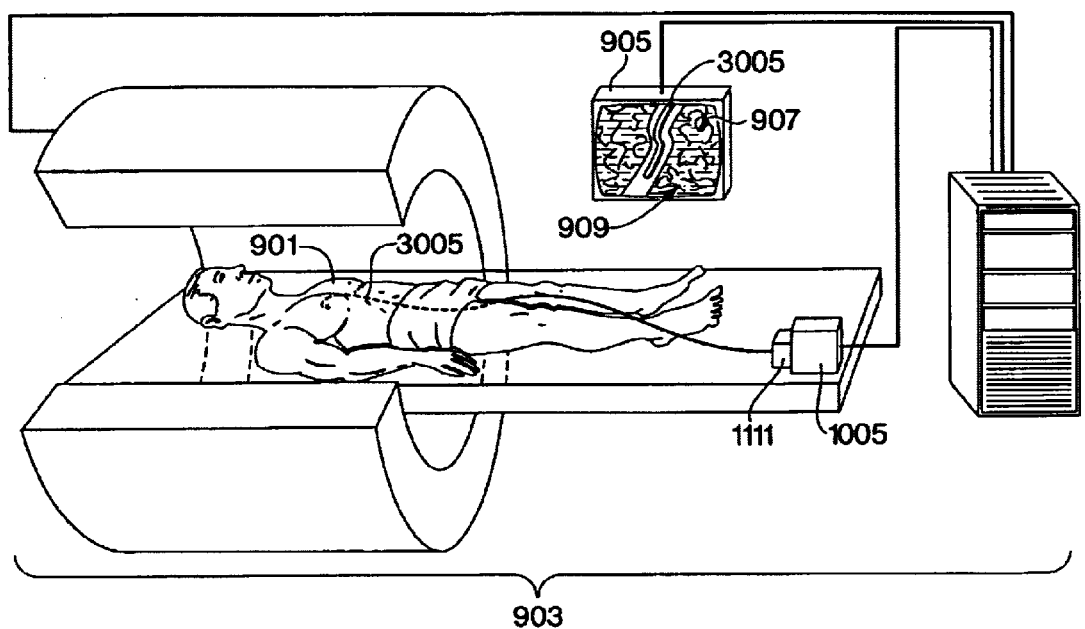
FIG. 27 shows a layout of a system of the instant invention wherein the guidewire probe might be used.

FIG. 27 shows one potential layout of a system whereby a guidewire probe could be used. In this figure, the subject 901 is shown within the MRI machine 903. The probe 3005 has been inserted into the subject 901. A display 905 is showing an MRI 907 showing the probe 3005 and the surrounding biological tissue 909. The probe 3005 is connected to the interface box 1005 through a connector 1111 that will allow a doctor (not shown) or another individual or machine to load or unload tools without removing the probe 3005 from the subject 901. The interface box 1005 is connected to the MRI machine 903 allowing the MRI machine 903 to use the probe 3005 as an active antenna in the subject 901.

While the invention has been disclosed in connection with the preferred embodiments shown and described in detail, various modifications and improvements thereon will become readily apparent to those skilled in the art. Accordingly, the spirit and scope of the present invention is limited only by the following claims.

What is claimed is:

1. A guidewire probe assembly suitable for receiving magnetic resonance signals from a sample, comprising:
   a probe shaft having a distal end and a proximate end, the probe shaft further comprising a core of non-magnetic material;

a first insulator or dielectric attached to said core;

a shielding disposed about at least a portion of said core; and an antenna attached to said distal end of said probe shaft, said antenna comprising a helical coil;

wherein at least said antenna is visible on a magnetic resonance image.

2. The guidewire probe assembly of claim 1, further comprising a second insulator or dielectric.

3. The guidewire probe assembly of claim 1, wherein said antenna comprises a substantially linear protrusion from said probe shaft.

4. The guidewire probe assembly of claim 3 wherein said substantially linear protrusion has a curve or hook at an end to facilitate engagement into a complex vessel.

5. The guidewire probe assembly of claim 3, wherein said helical coil comprises coils having a diameter and a spacing.

6. The guidewire probe assembly of claim 3, wherein said helical coil is disposed about said linear protrusion.

7. The guidewire probe assembly of claim 3, wherein said helical coil is electronically connected to said antenna, thereby increasing the electrical length of said antenna whip.

8. The guidewire probe assembly of claim 3, wherein said helical coil is not electrically connected to said antenna.

9. The guidewire probe assembly of claim 3, wherein said helical coil is attached to a distal end of said antenna.

10. The guidewire probe assembly of claim 3, further comprising a thin insulating material between said linear protrusion and said helical coil.

11. The guidewire probe assembly of claim 3 wherein said helical coil is electrically connected to said shielding.

12. The guidewire probe assembly of claim 5, wherein said diameter of said coils varies.

13. The guidewire probe assembly of claim 12, wherein said diameter of said coils is larger at said proximate end of said helical coil antenna than at said distal end of said helical coil antenna.

14. The guidewire probe assembly of claim 12, wherein said diameter of said coils is larger at said distal end of said helical coil antenna than at said proximate end of said helical coil antenna.

15. The guidewire probe assembly of claim 12, wherein said diameter of said coils is larger at at least one point between said proximate end and said distal end of said helical coil antenna than it is at at least one of said proximate or said distal end of said helical coil antenna.

16. The guidewire probe assembly of claim 12, wherein said diameter of said coils is smaller at at least one point between said proximate end and said distal end of said helical coil antenna than it is at at least one of said proximate or said distal end of said helical coil antenna.

17. The guidewire probe assembly of claim 5, wherein said spacing of said coils varies.

18. The guidewire probe assembly of claim 17, wherein said spacing of said coils is greater at said proximate end of said helical coil antenna than at said distal end of said helical coil antenna.

19. The guidewire probe assembly of claim 17, wherein said spacing of said coils is greater at said distal end of said helical coil antenna than at said proximate end of said helical coil antenna.

20. The guidewire probe assembly of claim 17, wherein said spacing of said coils is greater at at least one point between said proximate end and said distal end of said helical coil antenna than it is at at least one of said distal end of said helical coil antenna or said proximate end of said helical coil antenna.

21. The guidewire probe assembly of claim 17, wherein said spacing of said coils is less at at least one point between said proximate end and said distal end of said helical coil antenna than it is at at least one of said distal end of said helical coil antenna or said proximate end of said helical coil antenna.

22. The guidewire probe assembly of claim 1 wherein said helical coil has coils with a diameter and a spacing.

23. The guidewire probe assembly of claim 1 wherein said helical coil comprises at least one of copper, gold, silver, or aluminum wire.

24. The guidewire probe assembly of claim 1 wherein said antenna is covered by a biocompatible material or covering.

25. The guidewire probe assembly of claim 24 wherein the electrical length of said helical coil is chosen so as to compensate for said biocompatible material or covering.

26. The guidewire probe assembly of claim 1, wherein said helical coil is electrically connected to said core at least at one point.

27. The guidewire probe assembly of claim 22, wherein said diameter of said coils varies.

28. The guidewire probe assembly of claim 27, wherein said diameter of said coils is larger at said proximate end of said helical coil antenna than at said distal end of said helical coil antenna.

29. The guidewire probe assembly of claim 27, wherein said diameter of said coils is larger at said distal end of said helical coil antenna than at said proximate end of said helical coil antenna.

30. The guidewire probe assembly of claim 27, wherein said diameter of said coils is larger at at least one point between said proximate end and said distal end of said helical coil antenna than it is at at least one of said proximate or said distal end of said helical coil antenna.

31. The guidewire probe assembly of claim 27, wherein said diameter of said coils is smaller at at least one point between said proximate end and said distal end of said helical coil antenna than it is at at least one of said proximate or said distal end of said helical coil antenna.

32. The guidewire probe assembly of claim 22, wherein said spacing of said coils varies.

33. The guidewire probe assembly of claim 32, wherein said spacing of said coils is greater at said proximate end of said helical coil antenna than at said distal end of said helical coil antenna.

34. The guidewire probe assembly of claim 32, wherein said spacing of said coils is greater at said distal end of said helical coil antenna than at said proximate end of said helical coil antenna.

35. The guidewire probe assembly of claim 32, wherein said spacing of said coils is greater at at least one point between said proximate end and said distal end of said helical coil antenna than it is at at least one of said distal end of said helical coil antenna or said proximate end of said helical coil antenna.

36. The guidewire probe assembly of claim 32, wherein said spacing of said coils is less at at least one point between said proximate end and said distal end of said helical coil antenna than it is at at least one of said distal end of said helical coil antenna or said proximate end of said helical coil antenna.

37. The guidewire probe assembly of claim 1, wherein the total diameter of said guidewire probe is between about 0.010–0.040 inches.

38. The guidewire probe assembly of claim 1, wherein the total diameter of said guidewire probe is between $5/1000$ inch and 0.5 inch.

39. The guidewire probe assembly of claim 1, wherein said first insulator or dielectric comprises a low dielectric loss, low dielectric constant material.

40. The guidewire probe assembly of claim 1, wherein said guidewire probe is at least partially flexible.

41. The guidewire probe assembly of claim 1, wherein said guidewire probe is steerable inside a subject.

42. The guidewire probe assembly of claim 1, wherein said antenna is flexible.

43. The guidewire probe assembly of claim 1, wherein said antenna is loopless.

44. The guidewire probe assembly according to claim 1, further comprising a balun circuit.

45. The guidewire probe assembly of claim 44, wherein said balun circuit comprises a tuned balun circuit.

46. The guidewire probe assembly of claim 1, further comprising a helical coil placed around said probe shaft.

47. The guidewire probe assembly of claim 1, wherein said shielding comprises a helical coil.

48. The guidewire probe assembly of claim 1, wherein said probe shaft is tapered.

49. The guidewire probe assembly of claim 1, wherein said core of non-magnetic material is plated with alternating layers of gold and silver.

50. The guidewire probe assembly of claim 1, wherein said core of non-magnetic material is plated with a plurality of layers of conductive metal, said layers of conductive metal comprising one or more of the group of metals consisting of gold, silver, copper and aluminum.

51. The guidewire probe assembly of claim 1 wherein said core of non-magnetic material is fabricated from conductive metal comprising one or more, of the group of metals consisting of gold, silver, copper, MR-compatible stainless steel, and aluminum.

52. The guidewire probe assembly of claim 1, wherein said core of non-magnetic material comprises a super-elastic material.

53. The guidewire probe assembly of claim 52 wherein said super-elastic material comprises Nitinol.

54. The guidewire probe antenna assembly of claim 53, wherein said core of non-magnetic material is plated with alternating layers of gold and silver.

55. The guidewire probe assembly of claim 53, wherein said core of non-magnetic material is plated with a plurality of layers of conductive metal, said layers of conductive metal comprising one or more of the group of metals consisting of gold, silver, copper and aluminum.

56. The guidewire probe assembly of claim 1, wherein said core of non-magnetic material comprises a non-metallic material plated with a radio frequency conductive material.

57. The guidewire probe assembly of claim 56, wherein said core of non-metallic material comprises carbon.

58. The guidewire probe assembly of claim 56, wherein said core of non-metallic material comprises glass fiber.

59. The guidewire probe assembly of claim 56, wherein said core of non-metallic material comprises a polymer.

60. The guidewire probe assembly of claim 1, further comprising:

a connector portion for making an electrical connection between said guidewire probe and a mated connector portion electrically attached to an MRI machine.

61. The guidewire probe assembly of claim 60 whereby said connector enables loading and unloading interventional devices during a procedure without removal of said guidewire probe from a subject.

62. The guidewire probe assembly of claim 61 wherein said connector portion and said mated connector portion snap together.

63. The guidewire probe assembly of claim 61 wherein said mated connector portion clips to said connector portion.

64. The guidewire probe assembly of claim 61 wherein said mated connector portion can be locked by a screw portion in connection with said connector portion.

65. The guidewire probe assembly of claim 61 wherein said mated connector portion is screwably connected to said connector portion.

66. The guidewire probe assembly of claim 61 wherein said connector portion and said mated connector portion connect together in a manner which allows said guidewire probe to rotate freely without rotation of anything connected to said mated connector portion, but while maintaining electric contact between said connector portion and said mated connector portion.

67. The guidewire probe assembly of claim 61 wherein said connector portion and said mated connector portion connect together with a vice-like connection.

68. The guidewire probe assembly of claim 61 wherein said connector portion and said mated connector portion are not in direct electrical contact.

69. The guidewire probe assembly of claim 68 wherein signals are transmitted from said connector portion to said mated connector portion through the use of electromagnetic waves.

70. The guidewire probe assembly of claim 69 wherein said connector portion comprises a a solenoid coil.

71. The guidewire probe assembly of claim 69 wherein said mated connector portion comprises a solenoid coil.

72. The guidewire probe assembly of claim 69 wherein said connector portion comprises a loop coil.

73. The guidewire probe assembly of claim 69 wherein said mated connector portion comprises a loop coil.

* * * * *